(12) United States Patent
Hume et al.

(10) Patent No.: US 11,599,854 B2
(45) Date of Patent: *Mar. 7, 2023

(54) SYSTEMS AND METHODS FOR A GRAPHICAL INTERFACE INCLUDING A GRAPHICAL REPRESENTATION OF MEDICAL DATA

(71) Applicant: ICU Medical, Inc., San Clemente, CA (US)

(72) Inventors: James A. Hume, Deerfield, IL (US); Robert Mayer, Arlington Heights, IL (US); Devy Amy Lee, Round Lake Beach, IL (US); Gabriele Christensen, Bainbridge Island, WA (US); Candida Arvelo, Flower Mound, TX (US); Timothy L. Ruchti, Gurnee, IL (US); Tamas Ban, Round Lake Beach, IL (US); Mohammad M. Khair, Streamwood, IL (US); Nancy G. Hedlund, Libertyville, IL (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/225,911

(22) Filed: Apr. 8, 2021

(65) Prior Publication Data
US 2021/0295263 A1 Sep. 23, 2021

Related U.S. Application Data

(63) Continuation of application No. 16/584,466, filed on Sep. 26, 2019, now Pat. No. 11,004,035, which is a (Continued)

(51) Int. Cl.
*G16H 20/17* (2018.01)
*G06Q 10/10* (2023.01)
(Continued)

(52) U.S. Cl.
CPC ............ *G06Q 10/10* (2013.01); *G16H 10/60* (2018.01); *G16H 15/00* (2018.01); *G16H 20/17* (2018.01);
(Continued)

(58) Field of Classification Search
CPC ........ G16H 20/17; G16H 20/30; G16H 40/67; G16H 40/63; G16H 10/60; G16H 15/00;
(Continued)

(56) References Cited

U.S. PATENT DOCUMENTS 3,401,337 A 9/1968 Beusman et al.
3,484,681 A 12/1969 Grady, Jr. et al.
(Continued)

FOREIGN PATENT DOCUMENTS

AU 2013216679 9/2013
BR PI0704229-9 11/2009
(Continued)

OTHER PUBLICATIONS

Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.
(Continued)

*Primary Examiner* — Dino Kujundzic
(74) *Attorney, Agent, or Firm* — Knobbe, Martens, Olson & Bear, LLP

(57) ABSTRACT

This disclosure describes systems and methods for a graphical interface including a graphical representation of medical data. The graphical interface platform may receive medical data and provide medical safety reporting capabilities including reporting of history data and real-time visual monitoring data. The graphical interface platform may be configured to identify potential problems and corrections to
(Continued)

medical devices in operation while a reporting cycle is underway through visual representation of performance metrics.

18 Claims, 16 Drawing Sheets

Related U.S. Application Data continuation of application No. 14/973,236, filed on Dec. 17, 2015, now Pat. No. 10,430,761, which is a continuation of application No. 13/588,026, filed on Aug. 17, 2012, now Pat. No. 9,240,002.

(60) Provisional application No. 61/525,418, filed on Aug. 19, 2011.

(51) Int. Cl.
    *G16H 40/63*     (2018.01)
    *G16H 10/60*     (2018.01)
    *G16H 15/00*     (2018.01)
    *G16H 20/30*     (2018.01)
    *G16H 40/67*     (2018.01)
    *G16H 50/70*     (2018.01)
    *G16H 50/20*     (2018.01)

(52) U.S. Cl.
    CPC .............. *G16H 20/30* (2018.01); *G16H 40/63* (2018.01); *G16H 40/67* (2018.01); *A61M 2205/502* (2013.01); *A61M 2205/52* (2013.01); *G16H 50/20* (2018.01); *G16H 50/70* (2018.01)

(58) Field of Classification Search
    CPC ........ G16H 50/70; G16H 50/20; G06Q 10/10; A61M 2205/502; A61M 2205/52
    See application file for complete search history.

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,894,431 A | 7/1975 | Muston et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |

(56) References Cited

U.S. PATENT DOCUMENTS

| | | |
|---|---|---|
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,515,584 A | 5/1985 | Abe et al. |
| 4,519,792 A | 5/1985 | Dawe |
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Blomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,769,001 A | 9/1988 | Prince |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,908,019 A | 3/1990 | Urquhart et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |

(56) References Cited

U.S. PATENT DOCUMENTS

| | | |
|---|---|---|
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,014,798 A | 5/1991 | Glynn |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,260,665 A | 11/1993 | Goldberg |
| 5,257,206 A | 12/1993 | Hanson |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,304,216 A | 4/1994 | Wallace |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,749 A | 6/1995 | Merte et al. |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |

(56) References Cited

U.S. PATENT DOCUMENTS

| | | |
|---|---|---|
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,685,866 A | 11/1997 | Lopez |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Sternby |
| 5,733,259 A | 3/1998 | Valcke et al. |
| 5,734,464 A | 3/1998 | Gibbs |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A * | 7/1998 | Engleson ............... G16H 40/20 700/214 |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |

(56) References Cited

U.S. PATENT DOCUMENTS

| | | |
|---|---|---|
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,028,412 A | 2/2000 | Shine et al. |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,336,053 B1 * | 1/2002 | Beatty ............... G05B 19/4188 715/967 |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |

(56) References Cited

U.S. PATENT DOCUMENTS

| | | |
|---|---|---|
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B1 | 6/2003 | Lam et al. |
| 6,578,435 B2 | 6/2003 | Gould et al. |
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,606,047 B1 | 8/2003 | Börjesson et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouda et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |

(56) References Cited

U.S. PATENT DOCUMENTS

| | | |
|---|---|---|
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Girndt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| 7,338,470 B2 | 3/2008 | Katz |
| 7,347,836 B2 | 3/2008 | Peterson et al. |
| 7,347,854 B2 | 3/2008 | Shelton et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,477,997 B2 | 1/2009 | Kaplit |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,605,730 B2 | 10/2009 | Tomioka et al. |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenskow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,945,452 B2 | 5/2011 | Fathallah et al. |
| 7,976,508 B2 | 7/2011 | Hoag |
| 7,981,073 B2 | 7/2011 | Mollstam |
| 7,981,082 B2 | 7/2011 | Wang et al. |
| 7,998,134 B2 | 8/2011 | Row |
| 8,002,736 B2 | 8/2011 | Patrick et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,514 B2 | 12/2011 | Butterfield et al. |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blomquist |
| 8,175,668 B1 | 5/2012 | Nabutovsky et al. |
| 8,177,739 B2 | 5/2012 | Cartledge et al. |
| 8,180,440 B2 | 5/2012 | McCombie et al. |
| 8,185,322 B2 | 5/2012 | Schroeder et al. |
| 8,197,444 B1 | 6/2012 | Bazargan et al. |
| 8,219,413 B2 | 7/2012 | Martinez et al. |
| 8,221,395 B2 | 7/2012 | Shelton et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,409,164 B2 | 4/2013 | Row |
| 8,449,524 B2 | 5/2013 | Braig et al. |
| 8,469,942 B2 | 6/2013 | Kow et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,522,832 B2 | 9/2013 | Lopez et al. |
| 8,523,797 B2 | 9/2013 | Lowery et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |

(56) References Cited

U.S. PATENT DOCUMENTS

| | | |
|---|---|---|
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,728,020 B2 | 5/2014 | Caleffi et al. |
| 8,758,306 B2 | 6/2014 | Lopez et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,905,965 B2 | 12/2014 | Mandro et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |
| 9,190,010 B2 | 11/2015 | Vik et al. |
| 9,240,002 B2 | 1/2016 | Hume et al. |
| 9,272,089 B2 | 3/2016 | Jacobson et al. |
| 9,333,291 B2 | 5/2016 | Jacobson et al. |
| 9,381,296 B2 | 7/2016 | Arrizza et al. |
| 9,393,362 B2 | 7/2016 | Cozmi et al. |
| 9,468,718 B2 | 10/2016 | Hung et al. |
| 9,498,583 B2 | 11/2016 | Sur et al. |
| 9,545,475 B2 | 1/2017 | Borges et al. |
| 9,707,341 B2 | 7/2017 | Dumas, III et al. |
| 9,764,087 B2 | 9/2017 | Peterfreund et al. |
| 9,852,265 B1 | 12/2017 | Treacy et al. |
| 9,883,987 B2 | 2/2018 | Lopez et al. |
| 9,943,269 B2 | 4/2018 | Muhsin et al. |
| 9,995,611 B2 | 6/2018 | Ruchti et al. |
| 10,022,498 B2 | 7/2018 | Ruchti et al. |
| 10,046,112 B2 | 8/2018 | Oruklu et al. |
| 10,089,055 B1 | 10/2018 | Fryman |
| 10,099,009 B1 | 10/2018 | Anderson et al. |
| 10,166,328 B2 | 1/2019 | Oruklu et al. |
| 10,342,917 B2 | 7/2019 | Shubinsky et al. |
| 10,430,761 B2 | 10/2019 | Hume et al. |
| 10,463,788 B2 | 11/2019 | Day |
| 10,549,248 B2 | 2/2020 | Brown et al. |
| 10,578,474 B2 | 3/2020 | Ruchti et al. |
| 10,596,316 B2 | 3/2020 | Dumas, III et al. |
| 10,635,784 B2 | 4/2020 | Rubalcaba, Jr. et al. |
| 10,656,894 B2 | 5/2020 | Fryman |
| 10,682,102 B2 | 6/2020 | Declerck |
| 10,709,885 B2 | 7/2020 | Janders et al. |
| 10,850,024 B2 | 12/2020 | Day et al. |
| 10,874,793 B2 | 12/2020 | Oruklu et al. |
| 11,004,035 B2 | 5/2021 | Hume et al. |
| 11,029,911 B2 | 6/2021 | Fryman |
| 11,090,431 B2 | 8/2021 | Dumas, III et al. |
| 11,135,360 B1 | 10/2021 | Jacobson et al. |
| 2001/0007636 A1 | 7/2001 | Butterfield |
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |
| 2002/0013545 A1 | 1/2002 | Soltanpour et al. |
| 2002/0013551 A1 | 1/2002 | Zaitsu et al. |
| 2002/0015018 A1 | 2/2002 | Shimazu et al. |
| 2002/0016568 A1 | 2/2002 | Lebel et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0038392 A1 | 3/2002 | de la Huerga |
| 2002/0040208 A1 | 4/2002 | Flaherty et al. |
| 2002/0044059 A1 | 4/2002 | Reeder et al. |
| 2002/0045806 A1 | 4/2002 | Baker, Jr. et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0168278 A1 | 11/2002 | Jeon et al. |
| 2002/0173703 A1 | 11/2002 | Lebel et al. |
| 2002/0183693 A1 | 12/2002 | Peterson et al. |
| 2003/0009244 A1 | 1/2003 | Engleson |
| 2003/0013959 A1 | 1/2003 | Grunwald et al. |
| 2003/0018289 A1 | 1/2003 | Ng et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0052787 A1 | 3/2003 | Zerhusen et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158508 A1 | 8/2003 | DiGianfilippo |
| 2003/0160683 A1 | 8/2003 | Blomquist |
| 2003/0163789 A1 | 8/2003 | Blomquist |
| 2003/0173408 A1 | 9/2003 | Mosher, Jr. et al. |
| 2003/0186833 A1 | 10/2003 | Huff et al. |
| 2003/0187338 A1 | 10/2003 | Say et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0216682 A1 | 11/2003 | Junker |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |
| 2004/0119753 A1 | 6/2004 | Zencke |
| 2004/0120825 A1 | 6/2004 | Bouton et al. |
| 2004/0128162 A1 | 7/2004 | Schlotterbeck et al. |
| 2004/0128163 A1 | 7/2004 | Goodman et al. |
| 2004/0133166 A1 | 7/2004 | Moberg et al. |
| 2004/0145114 A1 | 7/2004 | Ippolito et al. |
| 2004/0147034 A1 | 7/2004 | Gore et al. |

(56) References Cited

U.S. PATENT DOCUMENTS

| | | |
|---|---|---|
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172289 A1 | 9/2004 | Kozic et al. |
| 2004/0172301 A1* | 9/2004 | Mihai ............... A61B 5/0002 705/2 |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0247445 A1 | 12/2004 | Nelson et al. |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0108057 A1 | 5/2005 | Cohen et al. |
| 2005/0119597 A1 | 6/2005 | O'Mahony et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0137653 A1* | 6/2005 | Friedman ............... A61B 5/742 607/60 |
| 2005/0143864 A1 | 6/2005 | Blomquist |
| 2005/0144043 A1 | 6/2005 | Holland et al. |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0197649 A1 | 9/2005 | Shelton et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0277911 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136095 A1 | 6/2006 | Rob et al. |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0180916 A1 | 8/2006 | Wyland |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229557 A1 | 10/2006 | Fathallah et al. |
| 2006/0229918 A1 | 10/2006 | Fotsch et al. |
| 2006/0235353 A1 | 10/2006 | Gelfand et al. |
| 2006/0255149 A1 | 11/2006 | Retter et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0265246 A1 | 11/2006 | Hoag |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0094045 A1 | 4/2007 | Cobbs et al. |
| 2007/0094046 A1* | 4/2007 | Cobbs ............... G16H 10/60 705/2 |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0156456 A1* | 7/2007 | McGillin ............... G16H 40/67 600/300 |
| 2007/0179436 A1 | 8/2007 | Braig et al. |
| 2007/0179437 A1 | 8/2007 | Grage et al. |
| 2007/0191817 A1 | 8/2007 | Martin |
| 2007/0214003 A1 | 9/2007 | Holland et al. |

(56) References Cited

U.S. PATENT DOCUMENTS

| | | |
|---|---|---|
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0250339 A1 | 10/2007 | Mallett et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0077116 A1 | 3/2008 | Dailey et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0169044 A1 | 7/2008 | Osborne et al. |
| 2008/0172030 A1 | 7/2008 | Blomquist et al. |
| 2008/0177254 A1 | 7/2008 | Shelton et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0200870 A1 | 8/2008 | Palmroos et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0243055 A1 | 10/2008 | Fathallah et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0099866 A1 | 4/2009 | Newman |
| 2009/0105636 A1 | 4/2009 | Hayter et al. |
| 2009/0112155 A1 | 4/2009 | Zhao |
| 2009/0114037 A1 | 5/2009 | Smith |
| 2009/0119330 A1 | 5/2009 | Sampath et al. |
| 2009/0124963 A1 | 5/2009 | Hogard et al. |
| 2009/0124964 A1 | 5/2009 | Leach et al. |
| 2009/0126825 A1 | 5/2009 | Eliuk et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0177992 A1 | 7/2009 | Rubalcaba et al. |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Mernoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2010/0022988 A1 | 1/2010 | Wochner |
| 2010/0280430 A1 | 1/2010 | Caleffi et al. |
| 2010/0036310 A1 | 2/2010 | Hillman |
| 2010/0056992 A1 | 3/2010 | Hayter |
| 2010/0057042 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0214110 A1 | 8/2010 | Wang et al. |
| 2010/0217154 A1 | 8/2010 | Deshmukh et al. |
| 2010/0217621 A1 | 8/2010 | Schoenberg |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0312039 A1 | 12/2010 | Quirico et al. |
| 2010/0317093 A1 | 12/2010 | Turewicz et al. |
| 2010/0317952 A1 | 12/2010 | Budiman et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0004620 A1 | 1/2011 | Butler et al. |
| 2011/0009797 A1 | 1/2011 | Kelly et al. |
| 2011/0028885 A1 | 2/2011 | Eggers et al. |
| 2011/0040247 A1 | 2/2011 | Mandro et al. |
| 2011/0046558 A1 | 2/2011 | Gravesen et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |

(56) References Cited

U.S. PATENT DOCUMENTS

| | | |
|---|---|---|
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0107251 A1 | 5/2011 | Guaitoli et al. |
| 2011/0137241 A1 | 6/2011 | DelCastilio et al. |
| 2011/0144595 A1 | 6/2011 | Cheng |
| 2011/0152770 A1 | 6/2011 | Diperna et al. |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0218514 A1 | 9/2011 | Rebours |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0313390 A1 | 12/2011 | Roy et al. |
| 2011/0319728 A1 | 12/2011 | Petisce et al. |
| 2011/0320049 A1 | 12/2011 | Chossat et al. |
| 2012/0025995 A1 | 2/2012 | Moberg et al. |
| 2012/0035535 A1 | 2/2012 | Johnson et al. |
| 2012/0059234 A1 | 3/2012 | Barrett et al. |
| 2012/0068001 A1 | 3/2012 | Pushkarsky et al. |
| 2012/0083760 A1 | 4/2012 | Ledford et al. |
| 2012/0089411 A1 | 4/2012 | Srnka et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0222774 A1 | 9/2012 | Husnu et al. |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2012/0310204 A1 | 12/2012 | Krogh et al. |
| 2012/0323212 A1 | 12/2012 | Murphy |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0032634 A1 | 2/2013 | McKirdy |
| 2013/0041342 A1 | 2/2013 | Bernini et al. |
| 2013/0044111 A1 | 2/2013 | VanGilder et al. |
| 2013/0083191 A1 | 4/2013 | Lowery et al. |
| 2013/0085443 A1 | 4/2013 | Lowery et al. |
| 2013/0085689 A1 | 4/2013 | Sur et al. |
| 2013/0110538 A1 | 5/2013 | Butterfield et al. |
| 2013/0150766 A1 | 6/2013 | Olde et al. |
| 2013/0150821 A1 | 6/2013 | Bollish et al. |
| 2013/0158504 A1 | 6/2013 | Ruchti et al. |
| 2013/0184676 A1 | 7/2013 | Kamen et al. |
| 2013/0197930 A1 | 8/2013 | Garibaldi et al. |
| 2013/0201482 A1 | 8/2013 | Munro |
| 2013/0218080 A1 | 8/2013 | Peterfreund et al. |
| 2013/0116649 A1 | 9/2013 | Kouyoumjian et al. |
| 2013/0253430 A1 | 9/2013 | Kouyoumjian et al. |
| 2013/0261993 A1 | 10/2013 | Ruchti et al. |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0345658 A1 | 12/2013 | Browne et al. |
| 2013/0345666 A1 | 12/2013 | Panduro et al. |
| 2014/0039446 A1 | 2/2014 | Day |
| 2014/0067425 A1 | 3/2014 | Dudar et al. |
| 2014/0145915 A1 | 5/2014 | Ribble et al. |
| 2014/0180711 A1 | 6/2014 | Kamen et al. |
| 2014/0224829 A1 | 8/2014 | Capone et al. |
| 2014/0267563 A1 | 9/2014 | Baca et al. |
| 2014/0303591 A1 | 10/2014 | Peterfreund et al. |
| 2014/0303754 A1* | 10/2014 | Nixon ............... G05B 23/0267 700/83 |
| 2014/0350513 A1 | 11/2014 | Oruklu et al. |
| 2014/0358077 A1 | 12/2014 | Oruklu et al. |
| 2015/0025453 A1 | 1/2015 | Ledford et al. |
| 2015/0033073 A1 | 1/2015 | Yang et al. |
| 2015/0065988 A1 | 3/2015 | Holderle et al. |
| 2015/0097701 A1 | 4/2015 | Al-Ali et al. |
| 2015/0168958 A1 | 6/2015 | Downie et al. |
| 2015/0224252 A1 | 8/2015 | Borges et al. |
| 2015/0246175 A1 | 9/2015 | Shubinsky et al. |
| 2015/0265765 A1 | 9/2015 | Yavorsky et al. |
| 2015/0338340 A1 | 11/2015 | Jiang et al. |
| 2015/0343141 A1 | 12/2015 | Lindo et al. |
| 2015/0371004 A1 | 12/2015 | Jones |
| 2016/0042264 A1 | 2/2016 | Borges et al. |
| 2016/0110088 A1 | 4/2016 | Vik et al. |
| 2016/0144101 A1 | 5/2016 | Pananen |
| 2016/0151560 A1 | 6/2016 | Toro et al. |
| 2016/0151562 A1 | 6/2016 | Magers et al. |
| 2016/0151601 A1 | 6/2016 | Cardelius et al. |
| 2016/0158437 A1 | 6/2016 | Biasi et al. |
| 2016/0175517 A1 | 6/2016 | Sileika et al. |
| 2016/0193604 A1 | 7/2016 | McFarland et al. |
| 2016/0256622 A1 | 9/2016 | Day et al. |
| 2016/0339167 A1 | 11/2016 | Ledford et al. |
| 2017/0043089 A1 | 2/2017 | Handler |
| 2017/0354941 A1 | 12/2017 | Brown et al. |
| 2018/0018440 A1 | 1/2018 | Sugawara |
| 2018/0028749 A1 | 2/2018 | Dumas, III et al. |
| 2019/0091401 A1 | 3/2019 | Ruchti et al. |
| 2019/0101425 A1 | 4/2019 | Ruchti et al. |
| 2019/0117890 A1 | 4/2019 | Oruklu et al. |
| 2019/0196770 A1 | 6/2019 | Fryman |
| 2019/0262535 A1 | 8/2019 | Shubinsky et al. |
| 2019/0269846 A1 | 9/2019 | Oruklu et al. |
| 2019/0282757 A1 | 9/2019 | Gylland et al. |
| 2020/0069864 A1 | 3/2020 | Shubinsky et al. |
| 2020/0113784 A1 | 4/2020 | Lopez et al. |
| 2020/0238007 A1 | 7/2020 | Day |
| 2020/0271499 A1 | 8/2020 | Ruchti et al. |
| 2020/0282137 A1 | 9/2020 | Dumas, III et al. |
| 2020/0324044 A1 | 10/2020 | Gylland et al. |
| 2020/0357500 A1 | 11/2020 | Rubalcaba, Jr. et al. |
| 2021/0170101 A1 | 6/2021 | Cavendish, Jr. et al. |
| 2021/0260283 A1 | 8/2021 | Oruklu et al. |
| 2021/0397396 A1 | 12/2021 | Fryman |
| 2022/0031943 A1 | 2/2022 | Dumas, III |

FOREIGN PATENT DOCUMENTS

| | | |
|---|---|---|
| CA | 2 113 473 | 3/1993 |
| CA | 2 551 817 | 7/2005 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |

(56) References Cited

FOREIGN PATENT DOCUMENTS

| | | |
|---|---|---|
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 1 490 131 | 12/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2010-063767 | 3/2010 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 01/033710 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/026420 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/028524 | 2/2013 |
| WO | WO 2013/036854 | 3/2013 |
| WO | WO 2013/096769 | 6/2013 |
| WO | WO 2014/004216 | 1/2014 |
| WO | WO 2015/134478 | 9/2015 |
| WO | WO 2017/051271 | 3/2017 |
| WO | WO 2017/144366 | 8/2017 |
| WO | WO 2017/197024 | 11/2017 |

(56) References Cited

FOREIGN PATENT DOCUMENTS

| WO | WO 2019/092680 | 5/2019 |
|---|---|---|
| WO | WO 2020/214717 | 10/2020 |
| WO | WO 2022/020184 | 1/2022 |

OTHER PUBLICATIONS

ALARIS® Medical Systems, "Signature Edition® GOLD—Single & Dual Channel Infusion System", San Diego, CA, USA, date unknown, but believed to be at least as early as Nov. 29, 2008, pp. 2-88 & 2-91.

Allegro, "3955—Full-Bridge PWM Microstepping Motor Drive", Datasheet, 1997, pp. 16.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsroom/press-releases/2014/05_08_14_sigma.page.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.

Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.

Buhrdorf et al., "Capacitive Micromachined Ultrasonic Transducers and their Application", Proceedings of the IEEE Ultrasonics Symposium, Feb. 2001, vol. 2, pp. 933-940.

Cannon, Md et al., "Automated Heparin-Delivery System to Control Activated Partial Thromboplastin Time", Circulation, Feb. 16, 1999, vol. 99, pp. 751-756.

"CareAware® Infusion Management", Cerner Store, as printed May 12, 2011, pp. 3, https://store.cerner.com/items/7.

Chen et al., "Enabling Location-Based Services on Wireless LANs", The 11th IEEE International Conference on Networks, ICON 2003, Sep. 28-Oct. 1, 2003, pp. 567-572.

Cheung et al., "Hyperglycemia is Associated with Adverse Outcomes in Patients Receiving Total Parenteral Nutrition", Diabetes Care, Oct. 2005, vol. 28, No. 10, pp. 2367-2371.

Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.

"Continually vs Continuously", https://web.archive.org/web/20090813092423/http://www.diffen.com/difference/Continually_vs_Continuously, as accessed Aug. 13, 2009 in 4 pages.

"CritiCore® Monitor: Critical Fluid Output and Core Bladder Temperature Monitor", BARD Urological Catheter Systems, Advertisement, 2005, pp. 2.

Daimiwal et al., "Wireless Transfusion Supervision and Analysis Using Embedded System", IEEE, 2010 International Conference ICBBT, China, Apr. 2010, pp. 56-60.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. http://archive.epo.org/epo/pubs/oj013/11_13/11_5033.pdf.

"Decision of the Administrative Council of Oct. 27, 2009 Amending the Implementing Regulations to the European Patent Convention (CA/D 20/09)", Official Journal EPO Dec. 2009, Dec. 2009, pp. 582-584. http://archive.epo.org/epo/pubs/oj009/12_09/12_5829.pdf.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

"Differential Pressure Transmitter, Series PD-39 X", SensorsOne Ltd., Advertisement, Dec. 2005, pp. 2.

Dunster et al., "Flow Continuity of Infusion Systems at Low Flow Rates", Anaesthesia and Intensive Care, Oct. 1995, vol. 23, No. 5, pp. 5.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

"Froth", http://www.merriam-webster.com/dictionary/froth, as accessed May 13, 2015 in 1 page.

Goldberg et al., "Clinical Results of an Updated Insulin Infusion Protocol in Critically Ill Patients", Diabetes Spectrum, 2005, vol. 18, No. 3, pp. 188-191.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

Hospira, "Plum A+™ Infusion System" as archived Dec. 1, 2012, pp. 2. www.hospira.com/products_and_services/infusion_pumps/plum/index.

Hospira, "Plum XL™ Series Infusion System" Technical Service Manual, Feb. 2005, Lake Forest, Illinois, USA, pp. i-vii, 5-14, 8-3.

Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.

Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.

International Preliminary Report on Patentability and Written Opinion received in PCT Application No. PCT/US2012/051300, dated Mar. 6, 2014 in 8 pages.

International Search Report and Written Opinion received in PCT Application No. PCT/US2012/051300, dated Oct. 19, 2012 in 9 pages.

JMS Co., Ltd., "Infusion Pump: OT-701", Tokyo, Japan, 2002, pp. 4.

Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.

Kutcher et al., "The Effect of Lighting Conditions on Caries Interpretation with a Laptop Computer in a Clinical Setting", Elsevier, Oct. 2006, vol. 102, No. 4, pp. 537-543.

Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.

Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.

Magaji et al., "Inpatient Management of Hyperglycemia and Diabetes", Clinical Diabetes, 2011, vol. 29, No. 1, pp. 3-9.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.

(56) References Cited

OTHER PUBLICATIONS

Merry et al., "A New, Safety-Oriented, Integrated Drug Administration and Automated Anesthesia Record System", Anesthesia & Analgesia, Aug. 2001, vol. 93, No. 2 pp. 385-390.

Microchip Technology Inc., "MTA11200B; TrueGauge™ Intelligent Battery Management I.C.", https://www.elektronik.ropla.eu/pdf/stock/mcp/mta11200b.pdf, 1995, pp. 44.

Moghissi, Etie, MD, FACP, FACE, "Hyperglycemia in Hospitalized Patients", A Supplement to ACP Hospitalist, Jun. 15, 2008, pp. 32.

Nuckols et al., "Programmable Infusion Pumps in ICUs: An Analysis of Corresponding Adverse Drug Events", Journal of General Internal Medicine, 2007, vol. 23, Supp. 1, pp. 41-45.

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.

SGS-Thomson Microelectronics, "L6219—Stepper Motor Drive", Datasheet, Dec. 1996, pp. 10.

SGS-Thomson Microelectronics, "PBL3717A—Stepper Motor Drive", Datasheet, Apr. 1993, pp. 11.

Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

Smith, Joe, "Infusion Pump Informatics", CatalyzeCare: Transforming Healthcare, as printed May 12, 2011, pp. 2.

Tang et al., "Linear Dimensionality Reduction Using Relevance Weighted LDA", Pattern Recognition, 2005, vol. 38, pp. 485-493, http://staff.ustc.edu.cn/~ketang/papers/TangSuganYaoQin_PR04.pdf.

Thomas et al., "Implementation of a Tight Glycaemic Control Protocol Using a Web-Based Insulin Dose Calculator", Anaesthesia, 2005, vol. 60, pp. 1093-1100.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Westbrook et al., "Errors in the Administration of Intravenous Medications in Hospital and the Role of Correct Procedures and Nurse Experience", BMJ Quality & Safety, 2011, vol. 20, pp. 1027-1034.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

\* cited by examiner

Welcome! John Smith
Security Level: Unrestricted
Role: Nursing, Historical
ADVANCED Mode   Logout

Dashboards

| Infusion (Text) | Infusion (Graph-Simple) | Infusion (Graph-Advanced) | ExecScoreCard | Pareto Tables | Rule Set Optimizer | Drug Library Optimizer |

High-level Infuser Information

| CCA | Pump Name | DL in use | Alert Status | Alarm Status | High-risk Med | Power Status |
|---|---|---|---|---|---|---|
| ICU | ICU_PCA-1 | Yes | PCA Avail. | None | YES | 100% |
| ICU | ICU_PlumA+_1 | No | NONE | Distal occlusion | YES | 100% (A/C) |
| ICU | ICU_Symbiq_1 | Yes | PCA locked out | None | YES | 25% |
| ICU | ICU_PCA_1 | Yes | NONE | Peridant fault | YES | 100% |
| ICU | ICU_PlumA+_1 | Yes | NONE | VTBI Complete | YES | 100% (A/C) |
| ICU | ICU_Symbiq_1 | Yes | NONE | Bag was empty | YES | 50% |
| ICU | ICU_PCA_1 | Yes | NONE | None | YES | 100% |
| ICU | ICU_PlumA+_1 | No | NONE | None | YES | 100% (A/C) |

Infuser Location and Infusion Therapy Information

| Asset No. | Pump Name | Medication | Concentration | Dose | Rate | VTBI | Volume Remaining | Rule Sets |
|---|---|---|---|---|---|---|---|---|
| W12300 | PCA | Morphine | 1 mg/mL | 5 mcg/kg/min | 8.4 mL/hr | 250 mL | 153 mL | Dose Rate |
| W12301 | PlumA+ | Dobutamine | 500 mg/250 mL | 1 mg/min | 33.3 mL/hr | 500 mL | 423 mL | Dose Rate |
| W12302 | PlumA+ | Amiodarone | 900 mg/500 mL | 2,000 Units/hr | 40 mL/hr | 500 mL | 230 mL | Dose Rate |
| W12303 | PlumA+ | Heparin | 25,000 Units/ 500 mL | 10 mEq/hr | 50 mL/hr | 50 mL | 27 mL | Dose Rate |
| W12304 | PlumA+ | KCL Rider 10 mEq | 10 mEq/50 mL | N/A | 400 mL/hr | 1,000 mL | 980 mL | Bolus Rate |
| W12305 | Symbiq | NaCl 0.9% | N/A | N/A | N/A | N/A | N/A | N/A |
| W12306 | PCA | N/A | N/A | N/A | N/A | N/A | N/A | N/A |
| W12307 | PlumA+ | Precedex | 200 mcg/50 mL | 0.5 mcg/kg/hr | 300 mL/hr | 50 mL | 24 mL | Dose Rate |

\*\*\*\* County General Hospital   1:34 PM   Current User: John Smith   Symbiq Drug Library Compliance: +9% ICU | +6% PEDS | -2% L&D | +14% PreOp   PlumA+ Drug Library

Dashboards

Welcome! John Smith
Security Level: Unrestricted
Role: Nursing, Historical
ADVANCED Mode    Logout

| Infusion (Text) | Infusion (Graph-Simple) | Infusion (Graph-Advanced) | ExecScoreCard | Pareto Tables | Rule Set Optimizer | Drug Library Optimizer |

CCA-ALL ▼  Infuser-ALL ▼           Infuser - ALL Scorecard         1/17/20 - 02/17/20

Summary

| DL Compliance | # of Total Programs | Total Alerts | Overrides | Edits | Upper Soft Limit Alerts | Lower Soft Limit Alert | Upper Hard Limit Alerts | Lower Hard Limit Alerts |
|---|---|---|---|---|---|---|---|---|
| 97.6% | 124,268 | 6,164 | 4,305 | 1,859 | 4,381 | 1,114 | 475 | 194 |

Total Alerts by Medication - Top 10 - Medications Infused

| Medication/Concentrations | Total Programs | Alerts | % Alerts to Programs | # Overrides | # Edits |
|---|---|---|---|---|---|
| IV Fluid | 33,852 | 2,177 | 6.4% | 1,786 | 391 |
| Heparin 25,000 Units/250 mL | 4,319 | 437 | 10.1% | 230 | 207 |
| Insulin 250 Units/250 mL | 3,295 | 69 | 2.1% | 42 | 27 |
| Propofol 1,000 mg/100 mL | 2,393 | 145 | 6.1% | 86 | 59 + |
| IVF - No Additives | 1,398 | 13 | 0.9% | 0 | 13 |
| IVF Fluid (50kg or more) | 1,392 | 145 | 10.4% | 127 | 18 |
| Potassium Chloride 20 mEq/50 mL | 1,107 | 139 | 12.6% | 115 | 24 |
| Antibiotic - Any Volume | 1,025 | 17 | 1.7% | 1 | 16 |
| Phenylephrine 10 mg/250 mL | 827 | 106 | 12.8% | 65 | 41 |

1%PEDS | 0% L&D | -2%

FIG. 9

Dashboards

| Infusion (Text) | Infusion (Graph-Simple) | Infusion (Graph-Advanced) | ExecScoreCard | Pareto Tables | Rule Set Optimizer | Drug Library Optimizer |

Infuser - ALL Scorecard

CCA-ALL ▼ | Infuser-ALL ▼

1/17/20 - 02/17/20

| Med/Conc ▼ | Alert Date/Time ▼ | Limit ▼ | Limit Violated ▼ | Initial Dose ▼ | Final Dose ▼ |
|---|---|---|---|---|---|
| Propofol 1,000 mg/100 mL | 03/31/20 02:08:29 | 75 mcg/kg/min | ↑UPPER SOFT | 80 | 80 |
| Propofol 1,000 mg/100 mL | 3/30/20 4:28:21 AM | 75 mcg/kg/min | -UPPER SOFT | 83 | 76 |
| Propofol 1,000 mg/100 mL | 2/2/20 11:16:30 PM | 75 mcg/kg/min | ↑UPPER SOFT | 79 | 79 |
| Propofol 1,000 mg/100 mL | 1/15/20 11:30:54 PM | 75 mcg/kg/min | -UPPER SOFT | 77 | 80 |
| Propofol 1,000 mg/100 mL | 12/29/20 6:00:53 AM | 75 mcg/kg/min | ↑UPPER SOFT | 79 | 76 |
| Propofol 1,000 mg/100 mL | 3/26/20 7:53:55 AM | 75 mcg/kg/min | -UPPER SOFT | 84 | 84 |
| Propofol 1,000 mg/100 mL | 8/12/20 2:23:26 PM | 75 mcg/kg/min | ↑UPPER SOFT | 84 | 80 |
| Propofol 1,000 mg/100 mL | 11/18/20 12:53:49 AM | 75 mcg/kg/min | -UPPER SOFT | 83 | 78 |
| Propofol 1,000 mg/100 mL | 4/24/20 5:27:10 PM | 75 mcg/kg/min | -UPPER SOFT | 82 | 77 |
| Propofol 1,000 mg/100 mL | 11/6/20 9:45:18 PM | 75 mcg/kg/min | -UPPER SOFT | 78 | 79 |
| Propofol 1,000 mg/100 mL | 1/16/20 | 75 mcg/kg/min | ↑UPPER SOFT | 81 | 78 |

FIG. 10

Dashboards

Summary

| DL Compliance | # of Total Programs | Total Alerts | Overrides | Edits | Upper Limit A... | Lower Hard Limit Alerts |
|---|---|---|---|---|---|---|
| 97.6% | 124,268 | 6,164 | 4,305 | 1,859 | 4,3... | 194 |

Infuser - ALL Scorecard  1/17/20 - 02/17/20

Total Alerts by Medication - Top 10 - Medications In...

| Medication/Concentrations | Total Programs | Alerts | % Alerts to Programs | # Overrides | # Edits |
|---|---|---|---|---|---|
| IV Fluid | 33,852 | 2,177 | 6.4% | 1,786 | 391 |
| Heparin 25,000 Units/250 mL | 4,319 | 437 | 10.1% | 230 | 207 |
| Insulin 250 Units/250 mL | 3,295 | 69 | 2.1% | 42 | 27 |
| Propofol 1,000 mg/100 mL | 2,393 | 145 | 6.1% | 86 | 59 |
| IVF - No Additives | 1,398 | 13 | 0.9% | 0 | 13 |
| IVF Fluid (50kg or more) | 1,392 | 145 | 10.4% | 127 | 18 |
| Potassium Chloride 20 mEq/50 mL | 1,107 | 139 | 12.6% | 115 | 24 |
| Antibiotic - Any Volume | 1,025 | 17 | 1.7% | 1 | 16 |
| Phenylephrine 10 mg/250 mL | 827 | 106 | 12.8% | 65 | 41 |

FIG. 11

Dashboards

Welcome! John Smith
Security Level: Unrestricted
Role: Nursing, Historical
ADVANCED Mode | Logout

| Infusion (Text) | Infusion (Graph-Simple) | Infusion (Graph-Advanced) | ExecScoreCard | Pareto Tables | Rule Set Optimizer | Drug Library Optimizer |

High-level Infuser Information

| CCA Name ▶ | Generic Name ▶ | Display Name ▶ | Medication Amount ▶ | Medication Unit ▶ | Diluent Amount ▶ | Diluent Unit ▶ | Dosi Uni |
|---|---|---|---|---|---|---|---|
| Anesthesia | maintenance IV | Maintenance Fluid | | | 1000 | mL | mL/k |
| Anesthesia | fentanyl | Fentanyl | 50 | mg | 1 | mL | mcg/k |
| Anesthesia | heparin | Heparin | 25000 | mcg | 500 | mL | Units/ |
| Anesthesia | insulin | Insulin | 100 | Units | 100 | mL | Units/ |
| Critical Care | insulin | Insulin | 100 | Units | 500 | mL | Units/ |
| MedSurg | heparin | Heparin | 25000 | Units | 500 | mL | Units/ |
| MedSurg | insulin | Insulin | 100 | Units | 500 | mL | Units/ |
| NICU 1.5 kg | fentanyl | Fentanyl | 250 | mcg | 100 | mL | mcg/k |
| OBGYN | heparin | Heparin | 25000 | Units | 500 | mL | Units/ |
| OBGYN | insulin | Insulin | 100 | Units | 100 | mL | Units/ |
| Oncology | heparin | Heparin | 25000 | Units | 500 | mL | Units/ |
| Oncology | insulin | Insulin | 100 | Units | 100 | mL | Units/ |
| Peds 10 kg | heparin | Heparin | 25000 | Units | 500 | mL | Units/ |
| Peds 10 kg | insulin | Insulin-DKA | 100 | Units | 500 | mL | Units/k |
| Peds 40 kg | heparin | Heparin | 25000 | Units | 500 | mL | Units/ |
| Peds 40 kg | insulin | Insulin-DKA | 100 | Units | 500 | mL | Units/k |
| Telemetry | heparin | Heparin | 25000 | Units | 500 | mL | Units/ |

The table represents Drugs from the Drug Library that are missing information (e.g. limits, overlaps, etc.). Please review each of the listed items.

Print

**** County General Hospital    1:36 PM    Current C

FIG. 13A

Dashboards

Welcome! John Smith
Security Level: Unrestricted
Role: Nursing, Historical
ADVANCED Mode    Logout

| Infusion (Text) | Infusion (Graph-Simple) | Infusion (Graph-Advanced) | ExecScoreCard | Pareto Tables | Rule Set Optimizer | Drug Library Optimizer |

High-level Infuser Information

| Display Name | Medication Amount | Medication Unit | Diluent Amount | Diluent Unit | Dosing Unit | LHL | LSL | USL | UHL |
|---|---|---|---|---|---|---|---|---|---|
| nance Fluid | 50 | mg | 1000 | mL | mL/hr | 1 | 5 | 250 | 999 |
| entanyl | 25000 | mcg | 1 | mL | mcg/kg/hr | | 0.01 | 4 | |
| Heparin | 100 | Units | 500 | mL | Units/hr | | 400 | 2500 | |
| sulin | 100 | Units | 100 | mL | Units/hr | | 0.25 | 10 | |
| sulin | 25000 | Units | 500 | mL | Units/hr | | 0.25 | 16 | |
| eparin | 100 | Units | 500 | mL | Units/hr | | 400 | 2500 | |
| sulin | 250 | mcg | 100 | mL | mcg/kg/hr | | 0.25 | 10 | |
| entanyl | 25000 | Units | 500 | mL | Units/hr | | 400 | 2500 | |
| Heparin | 100 | Units | 100 | mL | Units/hr | | 0.25 | 10 | |
| nsulin | 25000 | Units | 500 | mL | Units/hr | | 400 | 2500 | |
| Heparin | 100 | Units | 100 | mL | Units/hr | | 0.25 | 16 | 20 |
| nsulin | 25000 | Units | 500 | mL | Units/kg/hr | | 10 | 28 | |
| Heparin | 100 | Units | 500 | mL | Units/kg/hr | | 0.02 | 0.12 | 0.2 |
| sulin-DKA | 25000 | Units | 500 | mL | Units/kg/hr | | 10 | 28 | |
| Heparin | 100 | Units | 500 | mL | Units/kg/hr | | 0.02 | 0.12 | 0.2 |
| sulin-DKA | 25000 | Units | 500 | mL | Units/hr | | 400 | 2500 | |

The table represents Drugs from the Drug Library that are missing information (e.g. limits, overlaps, etc.). Please review each of the listed items.

nce: +9% ICU | +6% PEDS | -2% L&D | +14% PreOp   PlumA+ Drug Library Compliance: +3% ICU | +1%PEDS | 0% L&D | -2%

SYSTEMS AND METHODS FOR A GRAPHICAL INTERFACE INCLUDING A GRAPHICAL REPRESENTATION OF MEDICAL DATA

CROSS-REFERENCE TO RELATED APPLICATIONS

This application is a continuation of U.S. patent application Ser. No. 16/584,466, filed Sep. 26, 2019, which is a continuation of U.S. patent application Ser. No. 14/973,236, filed on Dec. 17, 2015, now U.S. Pat. No. 10/430,761, which is a continuation of U.S. patent application Ser. No. 13/588,026, filed on Aug. 17, 2012, now U.S. Pat. No. 9,240,002, which claims the benefit of priority of U.S. Provisional No. 61/525,418, filed Aug. 19, 2011. The content of each of the above applications are incorporated by reference herein in their entirety.

FIELD

This disclosure relates to representations and processing of medical data, and more particularly to, examples of graphical and textual displays of medical equipment data and data pertaining to a subject receiving treatment, monitoring or undergoing testing with electronic medical equipment.

BACKGROUND

Individual medical decision support platforms generally function independently without relying on performance optimizations derived from population specific data that is routinely collected. For example, decision support platforms may aggregate information into databases, but generally do not integrate the information or leverage knowledge gained to adapt and optimize therapy management rule sets and parameters to produce enhanced patient safety and patient outcomes.

A dashboard or user interface that adapts to user needs and provides information for treating patients in the presence of comparative analysis data with population performance under similar therapy rule sets and conditions may provide information useful to set alarms on outliers, and to flag outliers to staff for further investigation of inadequate response to therapy, for example.

Thus, an object of the present invention is the provision of a graphical user interface or dashboard system and methods that are useful to users or clinicians at various different levels in one or more healthcare facilities to monitor, manage and improve patient therapy conducted with electronic medical equipment.

This and other objects of the present invention will be apparent from the figures and the description that follows.

SUMMARY

This disclosure may disclose, inter alia, systems and methods for a graphical interface including a graphical representation of medical data such as medical equipment data and data pertaining to a subject receiving treatment, monitoring or undergoing testing with electronic medical equipment. The systems and methods provide real-time, near real-time, and summarized or trended historical information and analysis tools to various levels of interested parties in a healthcare environment.

Any of the methods described herein may be provided in a form of instructions stored on a non-transitory, computer readable medium, that when executed by a computing device, perform functions of the method. In some examples, each function may represent a module, a segment, or a portion of program code, which includes one or more instructions executable by a processor for implementing specific logical functions or steps in the process. The program code may be stored on any type of computer readable medium, for example, such as a storage device including a disk or hard drive. In addition, methods described herein may include one or more operations, functions, or actions that can be performed in a sequential order, performed in parallel, and/or in a different order than those described herein.

Further embodiments may also include articles of manufacture including a tangible computer-readable media that have computer-readable instructions encoded thereon, and the instructions may comprise instructions to perform functions of the methods described herein.

The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage medium.

In addition, circuitry may be provided that is wired to perform logical functions in processes or methods described herein.

In still other examples, functions described herein may be provided within a graphical interface platform. In these examples, the graphical interface platform may include a graphical user interface (GUI). A processor may execute software functions to create a data layout, and additional charts or graphs, on a display device. The display device may be configured to illustrate the graphical user interface, which may be configured to enable a user to analyze medical data in a visual display and accepts user inputs/instructions to illustrate selected data in a desired manner.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 3 illustrates an example screen shot of a configuration of a graphical interface.

FIGS. 5-6 illustrate an example screen shot of the graphical interface shown in FIG. 4 with additional associated information.

FIG. 9 illustrates an example screen shot of data compiled, sorted and ranked in a tabular format.

FIG. 10 illustrates an example screen shot of detailed "drill down" information associated with the interface in FIG. 9.

FIG. 11 illustrates an example screen shot of the interface in FIG. 9 filtered according to a date range.

FIGS. 13A-B are example screen shots of data available under a Rule Set Optimizer tab that shows high-level infuser information, such as drug library information for clinician review.

FIGS. 14-15 illustrate example screen shots of graphical representations indicating real-time and historical information associated with medical devices operating and therapy conditions. The data is filtered, compiled and displayed graphically for clinician review.

DETAILED DESCRIPTION

Figure 1:
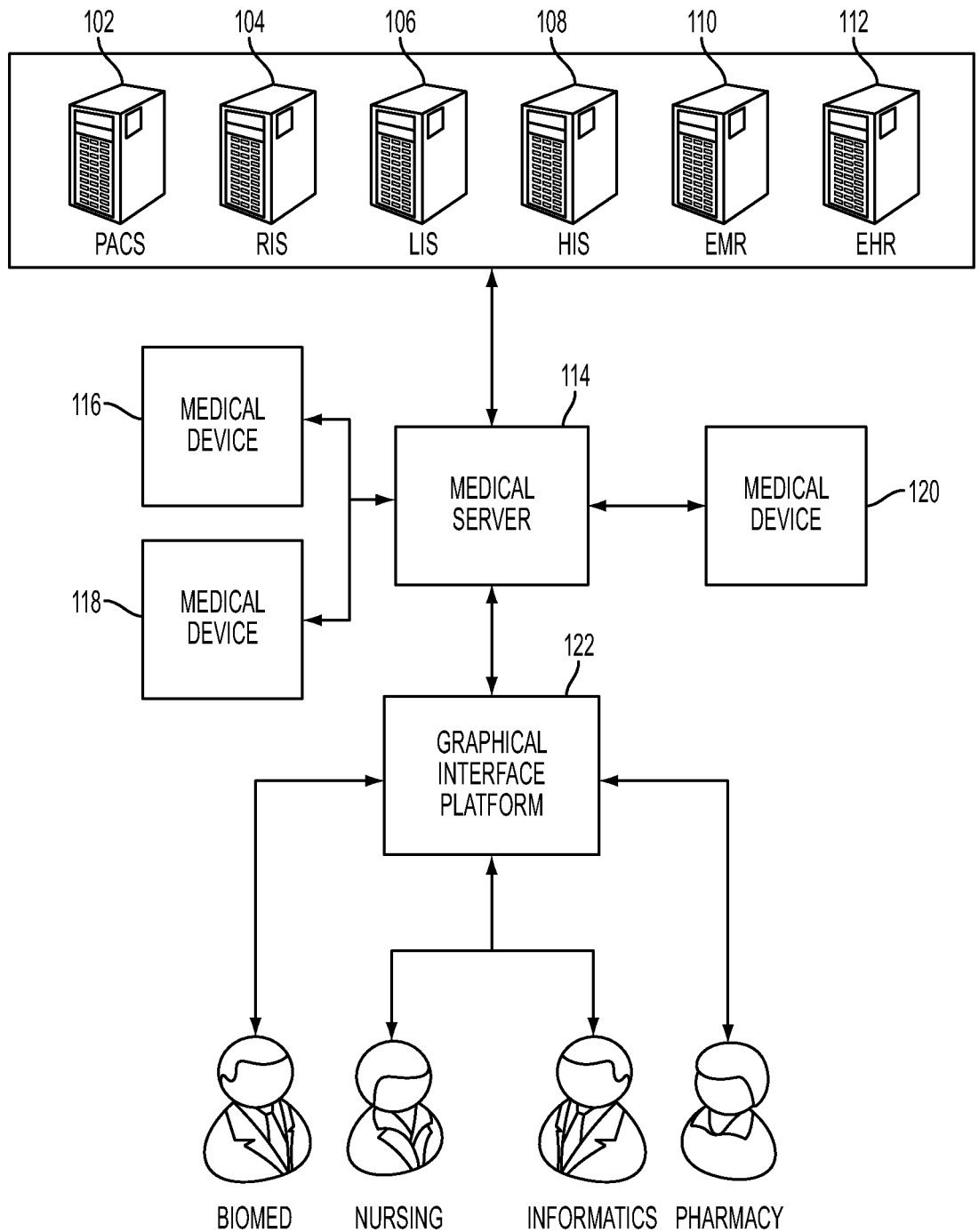
FIG. 1 illustrates an example system for receiving, processing, and providing medical data.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

This disclosure may disclose, inter alia, systems and methods for a graphical interface for providing medical data. The graphical interface may take the form of a graphical user interface (GUI), or of a real-time dashboard (RTD) software platform that is configurable on a user-by-user basis. The interface may be configured to provide contextually relevant data to a user. In some examples, the data may be based on a time frame (reporting intervals), on content (e.g., departments or clinical care areas of a hospital), prior usage patterns, or user type (e.g., pharmacist, nurse, physician, or quality assurance (QA) specialist). A base interval may include "real-time", for example, for a hospital environment in which a clinician may oversee ongoing medication administration. As organizational rank of a user increases, time increments may be expanded to longer (historical) periods of time to provide a higher level summary.

In the context of this disclosure, the terms "real-time", "near real-time" and "historical" are defined in relative terms. Real-time data is essentially current data that has been reported or communicated within about the past five seconds from the medical device, while near real-time data is current data that has been communicated within about the past five minutes, and historical data is previously reported data that was communicated at least about five minutes ago and more typically hours, days or longer ago. Historical data is a fairly easy concept to understand because such data was communicated a considerable time ago and therefore does not accurately reflect the current status of the medical device, nor the medication or patient associated with it. A user can analyze historical data for trends and to understand past activities, occurrences or performance, but would not believe the data to represent a current instantaneous status. However, the distinction between real-time and near real-time data is slipperier, blurrier, much harder to make, and depends greatly on the capabilities of the medical device, the communication network, and the graphical interface platform software to communicate, process, and populate all of the data on a particular graphic user interface screen or dashboard. Thus, the term real-time as used herein should be understood to more broadly include near real-time data as well, even when not specifically stated that way. Real-time data can be used for remote visual monitoring via the graphical interface platform to allow clinicians to locate medical devices, deliver medications to medical devices on a timely basis, and substantially immediately respond to alerts, alarms and other conditions of concern from medical devices or patients connected to the medical devices.

In some examples, the graphical interface platform may receive medical data and provide medical safety reporting capabilities including reporting of history data and real-time visual monitoring data. The graphical interface may be provided through an Internet or intranet interface, and can be made available to users on a restricted access basis.

In further examples, the graphical interface platform may be configured to identify potential problems and corrections to medical devices in operation while a reporting cycle is underway through visual representation of performance metrics.

The graphical interface platform may be a web-based user-by-user configurable real-time visual monitoring platform that provides contextually relevant and actionable data to the user. User adjustable filters can be provided to give the user an ability to drill down to identify potential actionable corrections as a result of alarms, alerts, infusion pump status, hard/soft limit overrides. Features include rules and/or algorithm engine, reporting, charting, drug library optimizer, and data aggregation of $3^{rd}$ party HIT data sources, and dashboard settings, user access and privileges can be determined based on area of use (e.g., nursing, pharmacy, or biomed).

Referring now to the figures, FIG. 1 illustrates an example system for receiving, processing, and providing medical data. The system includes a number of servers, such as a picture archiving and communication system (PACS) 102, a radiology information system (RIS) 104, a medical list server (LIS) 106, a hospital information system (HIS) 108, electronic medical records (EMR) 110, and electronic health records (EHR) 112, for example, that are coupled to a further medical server 114. The medical server 114 may further be coupled to a number of medical devices 116, 118, and 120, which may include any number of devices like infusion pumps, monitors, bedside computers, etc. The medical server 114 may be configured to receive information from the number of servers and medical devices, and provide the information to a graphical interface platform 122. Any number of users/clinicians, including without limitation nurses, doctors, hospital administrators, etc., who have different data needs, may access the graphical interface platform 122, and information provided on the graphical interface platform 122 can be configured accordingly.

The medical server 114 may process received information in a number of ways, and thus, may provide a number of functions including localized monitoring and control for hospital-created clinical care areas (CCAs), specific drug libraries and dosing recommendations based on hospital guidelines and industry best practices, determine hard and soft dosing limits to provide medication safety at the bedside for clinicians, allowing them to practice according to established best practices while allowing flexibility and adjustment for special patient populations as needed. In addition, within hospital-created guidelines, real-time monitoring of medication administration at the bedside, and real-time verification of the "5-Rights" may be provided. In one example, the medical server 114 may include or be configured to operate according to the Hospira MedNet™ server suite software, provided by Hospira of Lake Forest, Ill.

The graphical interface platform 122 may be configured to present centralized (server-based) medical device data (e.g., infusion pump data) to provide actionable data for continuous quality improvement (CQI) purposes to increase medication safety at the bedside and potentially reduce or avoid ADE's (adverse drug events). An example for such actionable data is referred to herein as an Executive Scorecard. Executive scorecards allow the clinicians (administration or medication safety committee) to view the highlights of past medication administration ("top ten" in different categories). Viewing these data highlights provides the clinician the ability to investigate and target medications causing the most problems (such as the most alerts, edits and overrides) for the clinicians or patients at the bedside. The success of resulting changes and adjustments to clinical practice can be monitored on an ongoing basis by reviewing the Executive Scorecard data. The graphical interface platform 122 may configure data to report occurrences when safety software is not being used and/or an alarm or alert is triggered (allowing for real-time intervention by the clinician at the bedside), identify alarm, alert or limit overrides, identify trends in clinical practice (how doctors are prescribing medications and how nurses are administering them), configure and optimize a "drug library" and rule sets that govern acceptable parameters related to a given medication/concentration in a specific clinical care area or CCA, or provide decision support/optimization tools for "smart" IV pumps. The graphical interface platform 122 also provides the ability for the clinician to perform ad hoc data analysis with the "drill-down" capability of the interface.

The graphical interface platform 122 may provide a Local Clinical Decision Support System (LDSS), which may provide information for advanced management of therapy with optional event alerting and notification and automation of decisions (e.g., therapy modification or suspension). For example, a probabilistic model, including Bayesian Decision Trees, may be employed, based upon prior population data, to identify specific adverse drug events, such as hypoglycemia. The graphical interface platform 122 may provide a dashboard of information that displays information on population behavior of patients with similar classifications or undergoing similar clinical therapies by presenting population summaries and comparing individual patients with relevant population outcomes. The dashboard may allow population comparative analysis to refine local decision support performance or produce alarms/alerts that are meaningful with respect to indicating population outliers. Information can be presented in real-time and may be relevant to current therapies administration. Furthermore, dashboards can also be used to monitor measured diagnostics, therapy outcomes, and decisions of multiple therapies decision support systems for the same patient.

The medical server 114 may provide access to the graphical interface platform 122 in real-time and via a web-interface. The graphical interface platform 122 may monitor a patient from a perspective of applied therapy, and may further represent inputs (medication infusion), outputs (physiological response), and medication sensitivity in a graphical manner. As a result, clinicians can view results of therapeutic decisions in real-time and identify individuals whose states are improving or degrading.

Information provided by the graphical interface platform 122 may be representative of information from Enterprise Clinical Decision Support Systems (EDSS) that can collect and further analyze information generated by Local Clinical Decision Support Systems (LDSS), such as glucose management or coagulation management. The EDSS can leverage knowledge of patient population performance under various therapy protocols to optimize the therapy rule sets and/or probabilistic models of local decision support systems. Patient population subgroups can be determined from patients with similar classifications using multiple parameters or characteristic of that population, for example, age, height, gender, weight, ethnicity, risk profile and clinical indication.

Therapy rule sets and algorithms that adapt therapy initialization using population specific information can be optimized using information derived from databases representing the patient population with relevant classification. Therapy initialization parameters include dose volume, boluses, starting infusion rates, timing of diagnostics measurements and patient specific information (e.g., demographics, medication allergies, lab values, and therapy histories).

The graphical interface platform 122 can provide predictive capabilities based on statistical sampling, clinical modeling and trend analysis. Comparative analysis can be made between a specific patient performance under a therapy protocol and remaining patient population subgroup on the same protocol, and alarms or alerts can indicate if this patient is an outlier from the general population that was treated under similar conditions and protocols. Statistical tools used to indicate outliers include box-car plots, decision trees, probabilistic models, cluster analysis, and abstract factor analysis, for example. Outlier patients may simply be part of a special patient population or may indicate a medication contraindication, or an interaction between multiple medications preventing the therapy protocol from achieving its expected effectiveness. Patient and population information can be presented in real-time and may be relevant to current therapies administrated. Speed to response is critical in some therapy protocols, allowing for real-time intervention at the bedside, preventing ADE's, patient harm and potentially saving lives.

Quality metrics can be provided and may be indicative of effectiveness of the adopted therapy protocols and safety metrics can also be collected to ensure therapy protocols are also safe.

Compliance metrics can also be collected and assess clinical practice and adherence to established "best practice" therapy protocols; preventing adverse outcomes and ADE's. Process control metrics such as six-sigma P-charts can be provided and may be indicative of how reproducible the desired measured outcomes are, and deviations from expected targets and acceptable ranges may indicate need for quality initiatives.

In some examples, the graphical interface platform 122 enables integration of information from multiple sources relevant to multiple therapies administered on the same patient such as therapy outcomes, medication allergies, medication history, orders, decisions, diagnostic lab values, vitals, etc., to allow for comprehensive dashboards to monitor and diagnose overall patient status and coordinate interaction between individual therapy protocols administered for more informed decision making. Coordinating multiple LDSS may produce managed and synchronized decisions to prevent undesired interactions and adverse events, optimize therapy decisions and allow for integration and documentation of information on sources of variability to an expected outcome of a particular LDSS.

Dashboards can further function to integrate information from multiple data sources, across heterogeneous hospital networks and information systems, and may aggregate and normalize databases and information, for example, such as combining multiple allergy definitions and vocabulary into a single standard definition (e.g., since medical terminology and uses are predominantly not standardized). A reference vocabulary database can be used along with a natural language processing engine to determine a context of use of terminology and eligibility for substitution, and the dashboard may automate selection of an appropriate reference vocabulary.

Dashboards can be further used to measure frequency of alerts, and alert loading per clinician, as well as workload per clinician, and average length of stay for patients as measures of quality of care. Other quality metrics can be designed to provide close to real-time monitoring of quality of operations. As an example, the dashboard may provide a patient event monitor that generates an alert when a change in patient condition has been detected on a basis of estimated internal control parameters (e.g., estimated medication sensitivity, compartmental volumes, and opioid efficacy). In some examples, the dashboard provides a model of the patient and detects a change in a condition of the patient on the basis of estimated internal parameters rather than observed measurements (e.g., vitals and labs).

In some examples, the graphical interface platform 122 may be configured to process information exchange between a plurality of local devices performing local decision support, and may benefit from population aggregated data to produce optimizations to the local decision support as well as indicate comparatively outliers from mainstream population outcomes as early alarms for need for intervention.

Figure 2:
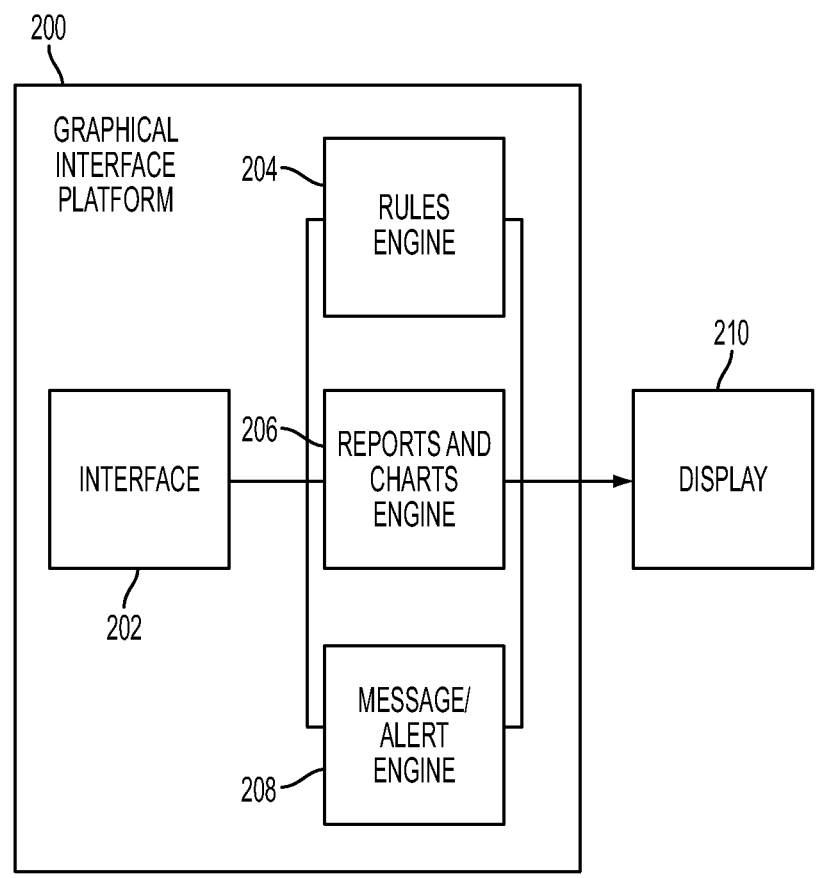
FIG. 2 is a block diagram of an example graphical interface platform.

FIG. 2 is a block diagram of an example graphical interface platform 200. The graphical interface platform 200 includes an interface 202, a rules engine 204, a reports and charts engine 206, a message/alert engine 208, and is coupled to a display 210.

The interface 202 may be a web-based interface enabling access by users via the Internet or intranet. Information provided to the display 210 may be based on a role-based view to enable context-relevant details (e.g., by discipline and detail level), and may provide user-specified customization of displayed data in a view.

The rules engine 204 may be configured to generate actionable notifications based on user-defined thresholds or internal decision models (e.g., decision trees, artificial neural network, Markov model, probabilistic networks, etc.) and route them to the user's preferred communication device (e.g., pager, cell phone, PDA, workstation, etc.). The reports and charting engine 206 may be configured to run ad hoc reports based on user-defined preferences. The message/alert engine 208 may be configured to route actionable notifications by email, pager, mobile phone, SMS, nurse station, central operator, etc., based on user preferences.

The graphical interface platform 200 may provide real-time visual monitoring of safety and operational metrics, real-time alerts that are pushed out to clinicians to enable immediate response, and trending/early warning indicators to identify opportunities for improvement. Information that is provided to the display 210 can be filtered based on a user customization, such as for nursing, pharmacy, biomed, risk management/quality, information technology, etc. Data from a number of servers (e.g., shown in FIG. 1) can be consolidated to provide patient-pump-caregiver visibility (for example from a barcode point of care or BPOC server), real-time location of pumps in facility (for example from a real-time location system or RTLS server), pump utilization and inventory versus hospital census (for example from an admissions-discharge-transfer system or ADT server), pumps requiring preventive maintenance (PM) or corrective action (computerized maintenance management system (CMMS), etc.

Furthermore, data may be output in a form of executive scorecards to allow c-level (Chief Information Officer, Chief Executive Officer, Chief Nursing Officer, etc.) hospital leaders to review actionable data, assess and leverage metrics and understand hospital performance as related to medication safety. Hospitals may produce scorecards "on-the-fly" to identify clinical trends in medication administration, deviations from established "best practices"—providing the needed focus for corrective interventions, assessing the effectiveness of such interventions in an effort to improve medication safety at the bedside and prevent ADE's and potential patient harm.

Each of the rules engine 204, the reports and charts engine 206, and the message/alert engine 208 may receive a set of parameters related to therapy objectives for a patient and thresholds for all input/output and calculated variables. Each of the rules engine 204, the reports and charts engine 206, and the message/alert engine 208 may include an input module that receives the infusion information and diagnostic response, a calculation module that models the input/output or I/O relationship between the medication infusion and diagnostic response, a database for accumulating calculated parameters specific to the calculation module, a decision module that monitors inputs, outputs and calculated parameters and detects changes in any or all of the three categories, and an alert capability that is set when a change has occurred.

The calculation module may include a single multivariate model, such as used with time varying parameters or probabilistic network, that are adjusted based upon data and clinician input using maximum likelihood optimization, structured optimization (e.g., genetic or hill-climbing algorithms), an extended Kalman filter, Bayesian estimator based upon input/output data. The calculation module may also include a mixture of single models operating in parallel. The individual models are weighted or prioritized based upon prediction error. In addition the models can be used for prediction and analysis of possible outcomes. The calculation module may further include other multiple models, in which a group of static models can be used to identify patient responses and the group of models with a lowest prediction error through time can be selected for analysis.

The graphical interface platform 200 may be configured to model patient therapy and response dynamics and detect a change in condition of the patient on the basis of internal parameters. The rules engine 204, the reports and charts engine 206, and the message/alert engine 208 may provide predictions of future physiological variables and risk metrics for display on the dashboard. The graphical interface platform 200 may be further configured to model therapy alternatives and select an objective that best suits the therapy objective. Therapy objectives can be selected based on time to reach targets or safety, such as avoiding medication interactions, optimizing medication delivery profiles, minimizing the risk of an adverse outcome or reducing cost of therapy.

The graphical interface platform 200 may be configured to operate on a computing device. Alternatively, a computing device may be configured to provide the graphical interface platform 200. The computing device may be a personal computer, mobile device, cellular phone, tablet computer, etc., and may be implemented to provide the graphical interface platform including a graphical representation as shown in any of FIGS. 3-15 described below. In one configuration, a computing device may include one or more processors and system memory that includes one or more applications and program data. The computing device may be configured to execute instructions to perform functions of the graphical interface platform. The instructions may be implemented as computer program instructions encoded on a non-transitory computer-readable storage media in a machine-readable format, or on other non-transitory media or articles of manufacture.

FIGS. 3-15 illustrate example screen shots of a graphical interface platform as a dashboard program. In these examples, the graphical interface platform is provided as a graphical user interface (GUI). Thus, a processor may execute software functions to create a data layout, and additional charts or graphs, on a display device. The display device 210 (FIG. 2) illustrates the graphical user interface, which enables a user to analyze medical data in a visual display and accepts user inputs/instructions to illustrate selected data in a desired manner. The graphical user interface (GUI) may be of a standard type of user interface allowing a user to interact with a computer that employs graphical images in addition to text to represent information and actions available to the user. Actions may be performed through direct manipulation of graphical elements, which include windows, buttons, menus, and scroll bars, for example.

A user name and password may be required to access the dashboard program. If the password or user is not recognized based on a database of eligible users, the user cannot continue to the next screen. Based on the user identification numbers, users can be assigned various privileges and rights, which allow access to view various data with various granularities. For example, based on organizational hierarchy, levels and qualifications of the user (e.g., bedside nurse versus facility supervisor/charge nurse versus Chief Nursing Office or CNO versus Pharmacist), different types and details of relevant information may be shown. The type and amount of information may be customizable per user, user type, or privilege status.

The example screen shots in FIGS. 3-15 illustrate medical data pertaining to infusion pumps; however, the medical data may be related to or received from any number of other medical devices.

FIG. 3 illustrates an example screen shot of a configuration of the dashboard. The dashboard includes many tabs such as: Infusion (Text), Infusion (Graph-Simple), Infusion (Graph-Advanced), ExecScoreCard, Pareto Tables, Rule Set Optimizer, Drug Library Optimizer. Data of the first tab ("Infusion (Text)") is illustrated in FIG. 3 displaying text-based "High-level Infuser Information", such as "CCA", device type or name ("Pump Name"), Drug Library compliance or usage ("DL in use"), "Alert Status", "Alarm Status", high-risk medication indication ("High-risk Med"), and "Power Status" by way of example and not limitation. In addition, the dashboard provides "Infuser Location and Infusion Therapy Information" including but not limited to infuser "Asset No." as shown and "Location" (not shown), as well as infusion therapy information such as Pump Name, "Medication", "Concentration", "Dose", "Rate", programmed volume to be infused ("VTBI"), "Volume Remaining" in the container or of the programmed VTBI, "Rule Sets" that are being employed, etc. A user may scan through all pumps that are online and infusing, view real-time alerts/alarms or power status. The data in the Alert Status and Alarm Status cells provide immediate information and feedback to the clinician, allowing for real-time decision making and prioritization. Filters can be applied to include or exclude certain devices, events or specific criteria. Alerts are typically informative in nature, whereas alarms can indicate situations requiring immediate intervention to not delay therapy, i.e., a distal occlusion caused the device to alarm and stop the infusion. Flashing text, special symbols, or colors such as red, yellow, orange, etc. can be used to better draw the user's attention to alarms or alerts if the status is something other than "none". The delivery of high-risk medications is specifically shown and/or highlighted on the dashboard to allow for greater focus when monitoring medication administration for a whole unit or clinical care area. The power status indicates if the pump is currently powered by a battery or A/C power source, and the current amount of power or battery capacity remaining, which can be expressed as a percentage. If the pump is currently plugged into an A/C power source, a default value of 100% is displayed for power status, but the actual remaining capacity of the battery while it is recharging can be displayed alternatively or in addition thereto. The data shown on this page may be received from Hospira Med-Net™ software. The user may print this screen to a printer using the "Print" button shown in the upper right corner area of the screen. The display of the infuser location is pertinent in tracking devices for purposes of recall, maintenance, installation, Drug Library update, etc. The infuser location may be useful for dispensing and delivering an additional full IV bag to a proper pump. For example, a pharmacy may dispense another bag and deliver it to the correct location.

Figure 4:
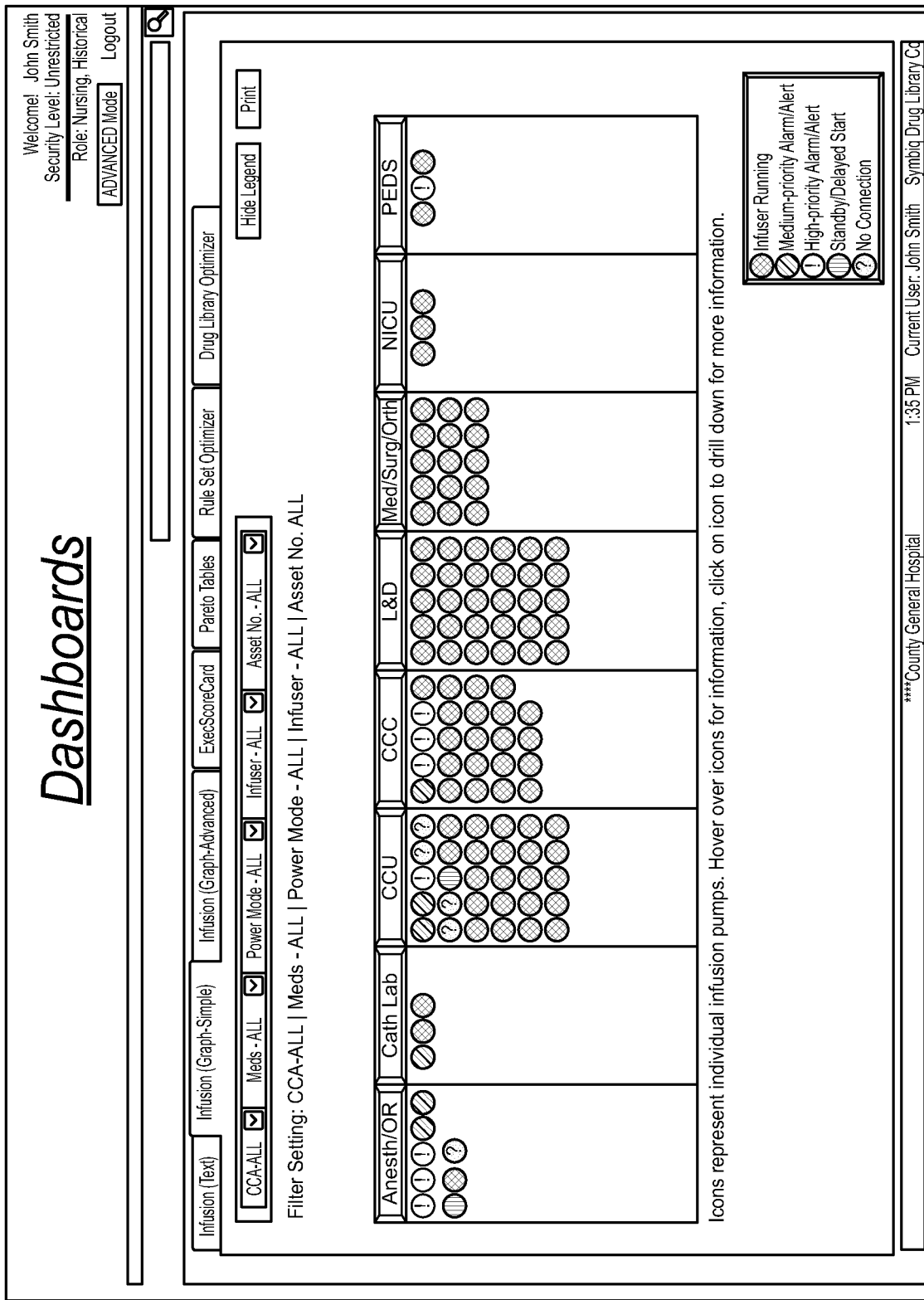
FIG. 4 illustrates an example screen shot of data in a graphical interface in a Graph-Simple form.

In addition, the graphical interface may associate a medical device to a patient based on a location of the medical device and/or based on a location of the patient. An example screen shot of data of the second tab ("Infusion (Graph-Simple)") is shown in FIG. 4. Each icon in the illustration may represent a medical device (e.g., an infusion pump). The icon shown in the example of FIG. 4 is a circular dot that may be filled in with certain colors, symbols, and text or display characteristics. A circular dot is beneficial in that a great number of distinct medical devices or pumps can be clearly shown for one or more clinical care areas in a small amount of space on the screen. However, other icons with different shapes, colors, and text and display characteristics can be utilized without detracting from the invention. The icon could be an actual image of an infusion pump system or a simplified pictorial representation of key aspects of the pump system such as the battery or power bus, container(s) the pump is drawing from, patient the pump is connected to, etc. See FIGS. 7 and 8 for examples of simplified pictorial representations of a plurality of pumping systems on the dashboard. Referring again to FIG. 4, the colors and symbols on the dots convey information about a status of the infuser (e.g., green if infuser is running, yellow if there is a medium-priority alarm/alert, red with an optional exclamation point inside if there is a high-priority alarm/alert, blue if the infuser is on a standby or delayed start, or gray with an optional question mark inside if the infuser is offline or not connected to the network, etc.). The representations of the colors and symbols can be included in a legend at a bottom of the dashboard screen, as illustrated in FIG. 4. Each column may represent an area in a hospital, which may be filtered using a pull-down menu by a user. Further filters are provided to filter pumps to be displayed by area, medication type in general or medication type by category (high-risk or low-risk, antibiotics, etc.), power mode (infuser running on batteries or A/C), types of infuser (e.g., PLUM A+™, SYMBIQ™, LIFECARE PCA™, SMITHS MEDICAL MEDFUSION™, ALARIS MEDLEY™, B. BRAUN OUTLOOK™, SIGMA™, etc.), and Asset No. (and/or serial number, MAC address, IP address, wired or wireless access node, etc.).

Figure 5:
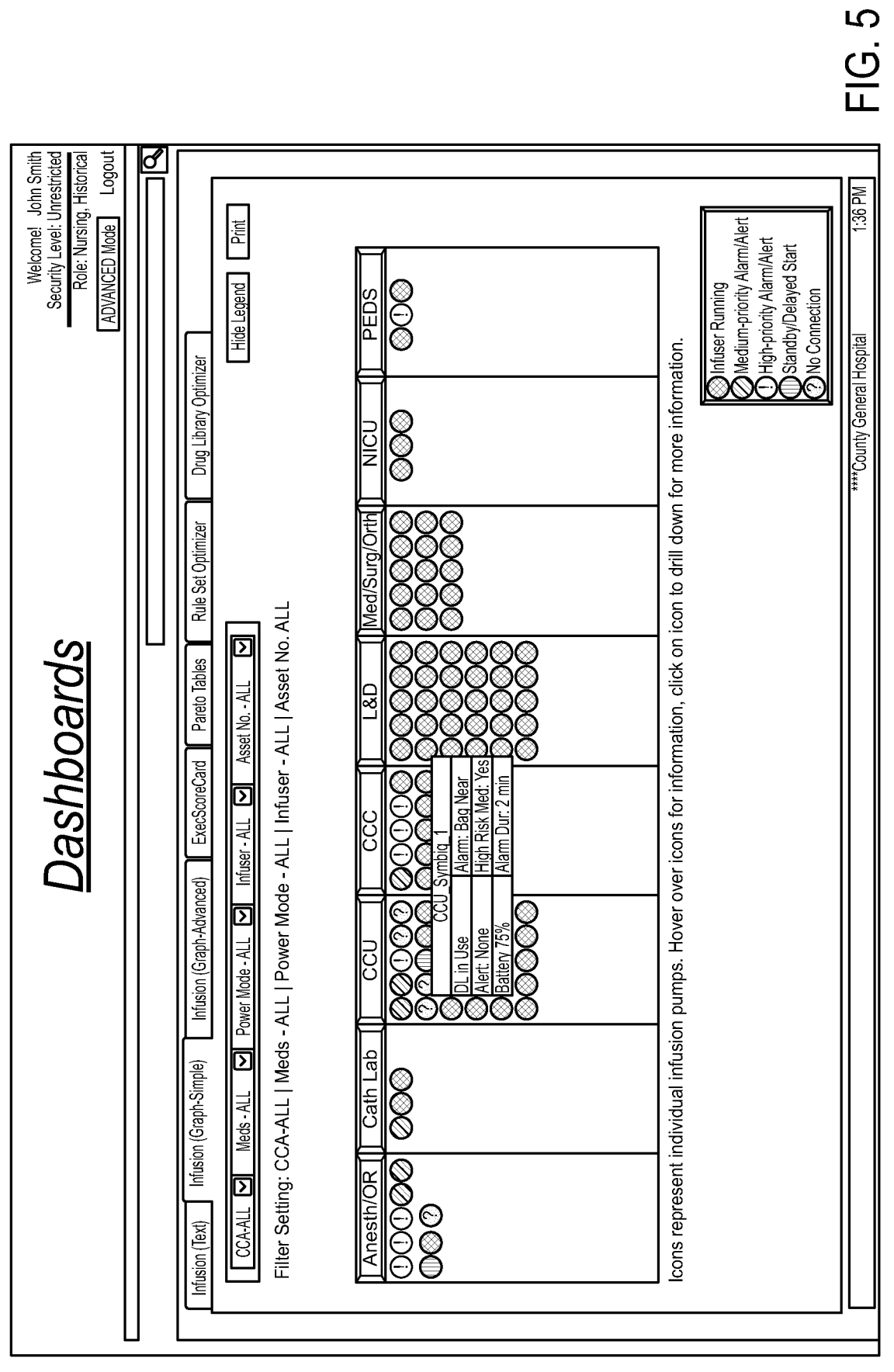
Figure 6:
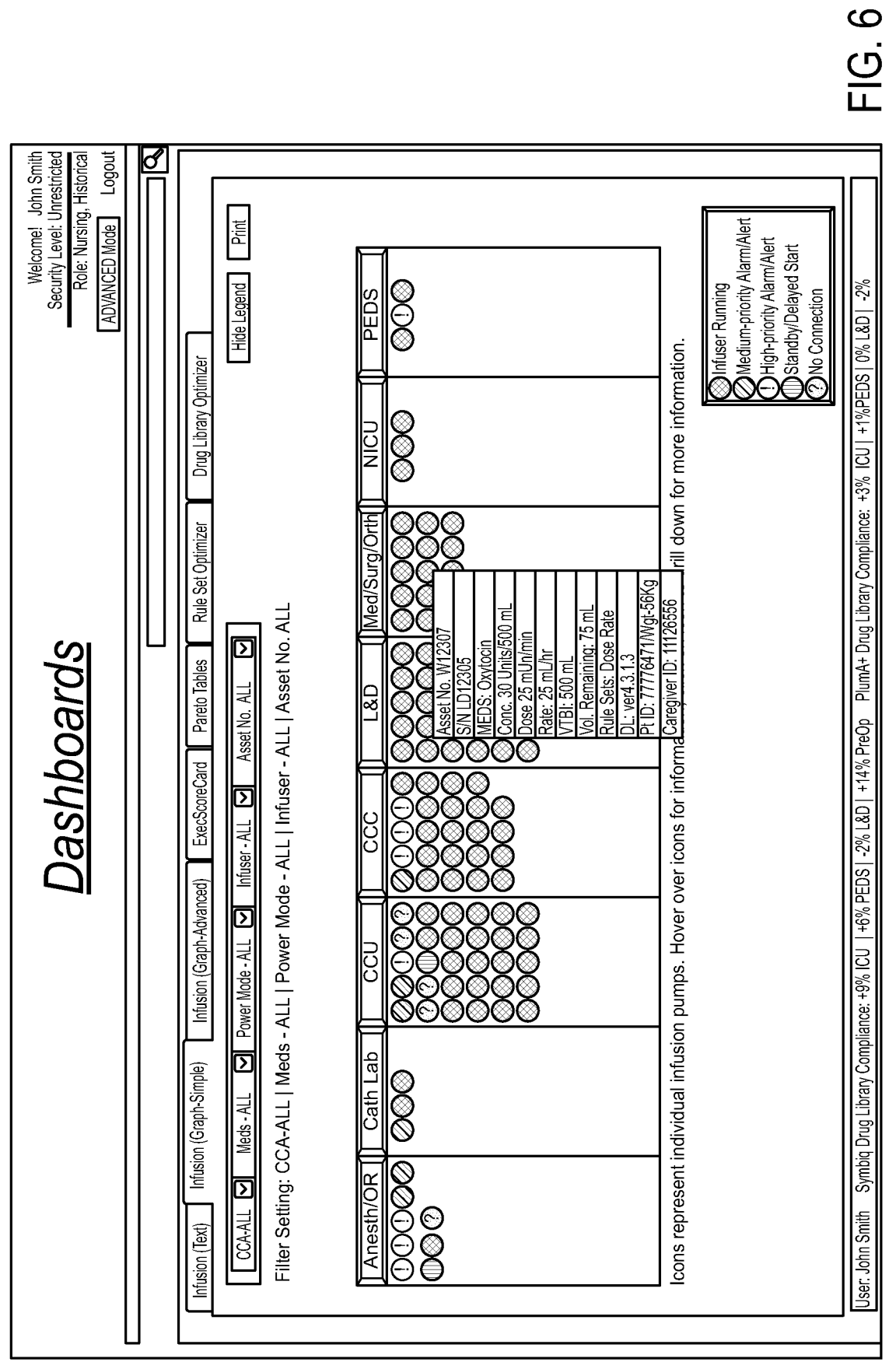

Using a cursor or pointer device, hovering over a dot may provide additional information, such as shown in FIGS. 5-6, including a pump's current status, ID, caregiver ID, etc. For example, a user may hover-over an icon to cause the graphical representation to produce a pop-up screen containing more specific information on the medical device including infuser name, whether the drug library is in use, alert status, battery life, alarm status (here an IV container or bag the pump is drawing from is nearly empty), whether the infuser is infusing a high-risk medication, if there was an alarm/alert and length of time the incident has gone unresolved, etc. As seen in FIG. 6, for example, using a mouse, a user may click-down on an icon to cause the graphical user interface to search for more information on the medical device including asset number, serial number, medication, concentration, dose, rate, volume to be infused (VTBI), volume remaining, rules sets, drug library, patient identification number, caregiver information, etc.

Figure 7:
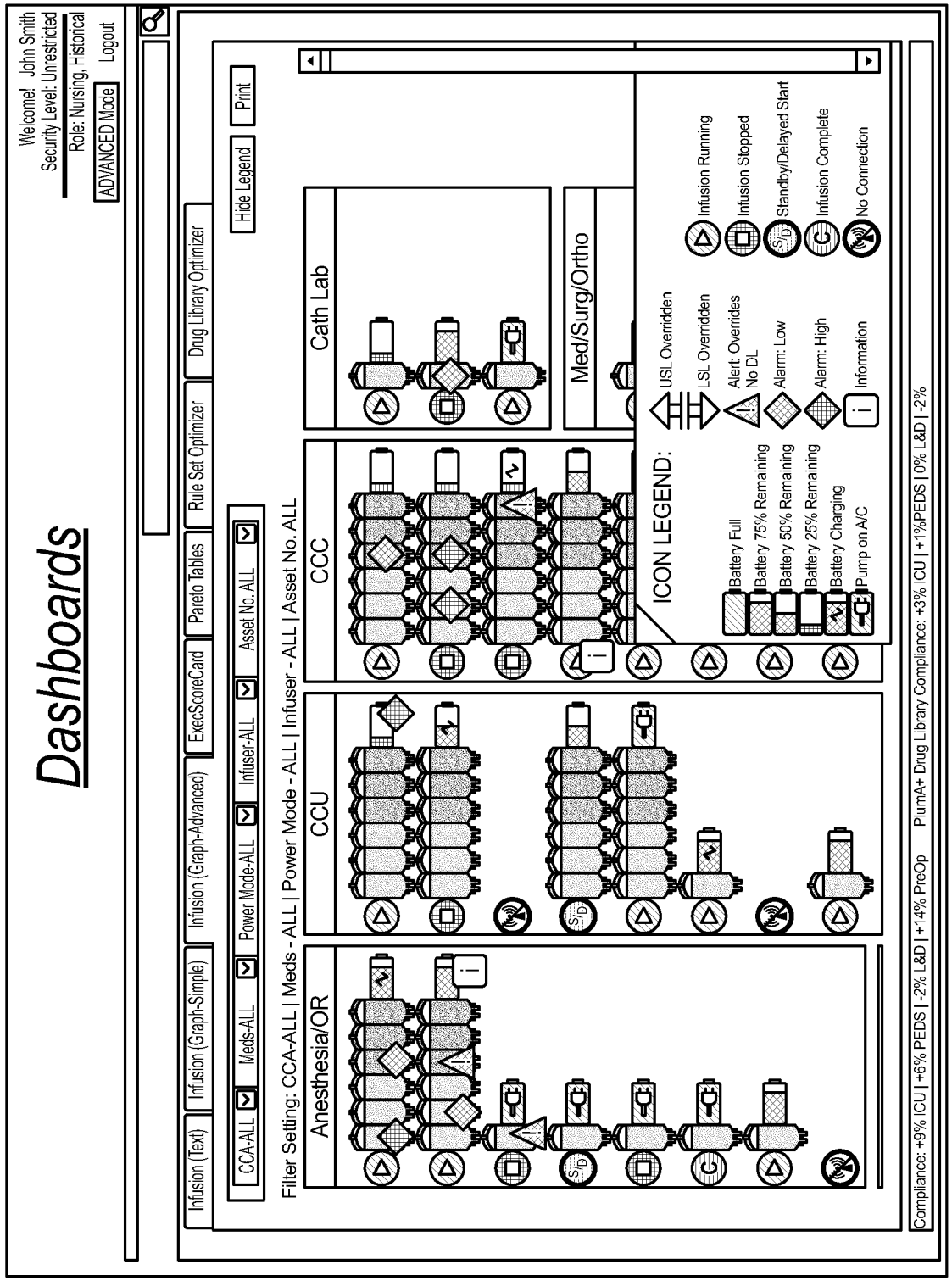
FIG. 7 illustrates an example screen shot of data in a graphical interface in a more detailed "drilled down" graphical format.

An example screen shot of the "Infusion (Graph-Advanced)" tab is shown in FIG. 7. Data illustrated on this page may be filtered in the same manner as previously described. Each line or horizontal section in the illustration may graphically represent an infusion pump (or single infuser), and each column in the illustration may graphically represent a clinical care area or CCA. Alternatively each line of the illustration may represent a multi-channel infusion pump system that includes a plurality of infusers or infusion channels associated with a common support structure or patient. Information contained graphically for each infuser on the horizontal lines include infuser status (e.g., a green dot with optional white, right-facing triangle inside for an infusion running, a red dot with optional square inside for infusion stopped, a red outlined circle with optional gray fill and white "S/D" text inside for standby/delayed start, a blue dot with an optional white "C" inside for infusion complete, and a red outlined dot with an optional diagonal red backslash striking through a wireless symbol for infuser offline or no connection), notification (e.g., a yellow triangle with an optional exclamation point inside for an alert such as no drug library present or in use (this is sometimes referred to as drug library "compliance"), a yellow up arrow indicates that the operator has overridden an upper soft limit, a yellow down arrow indicates that the operator has overridden a lower soft limit, or pump operator, a yellow diamond for low concern or priority alarms, a red diamond for high concern or priority alarms, and a white square with an optional "i" inside for general information), and power status (e.g., battery images colored and shaded or proportionally filled so as to depict battery conditions such as battery full (100% green), battery 75% remaining (75% yellow), battery 50% remaining (50% yellow), battery 25% remaining (25% red), a battery image with a charging symbol inside to indicate the battery is charging, a battery image with a symbol or picture of an A/C plug inside to indicate the pump or infuser is operating on A/C).

Each line-item representation of an infuser under a specific clinical care area indicates in real-time the current status of the pump, container information, and battery information. A number of bag/container icons are used to indicate how many containers are being administered by the infusion pump. By way of example, for a three-channel infusion pump system that can deliver from two containers per channel in an alternating sequence or simultaneously, up to six total bags/containers are shown in FIG. 7 to graphically illustrate pump-status, alarms, alerts, container status, etc. Thus, infusion pumps with single pumping channels or pumps with multiple pumping channels can be illustrated. Information from infusion pump systems including single or multiple channel infusion pumps in combination with other medical devices can be illustrated as well. For example, a pump and a physiological monitor or meter such as a pulse oximeter (SpO2), capnography (ETCO2) meter or glucometer can be included in the pump system and illustrated by the dashboard. When multiple containers are ordered for the patient, a graphic depiction or icon of a container in waiting can be provided above, below, or partially behind the icon for container in use. The user can filter the information based on: clinical care area, medication type (high-risk or low-risk), power mode (infuser running on batteries or A/C), infuser type (e.g., PLUM A+™, SYMBIQ™, LIFECARE PCA™, SMITHS MEDICAL MEDFUSION™, ALARIS MEDLEY™, B. BRAUN OUTLOOK™, SIGMA™, etc.), and Asset No. (or serial number, MAC address, IP address, wired or wireless access node, etc.). Data illustrated in FIG. 7 is provided using graphical icons to enable an easy to use, quick, visual, intuitive illustration of the data for a user.

Figure 8:
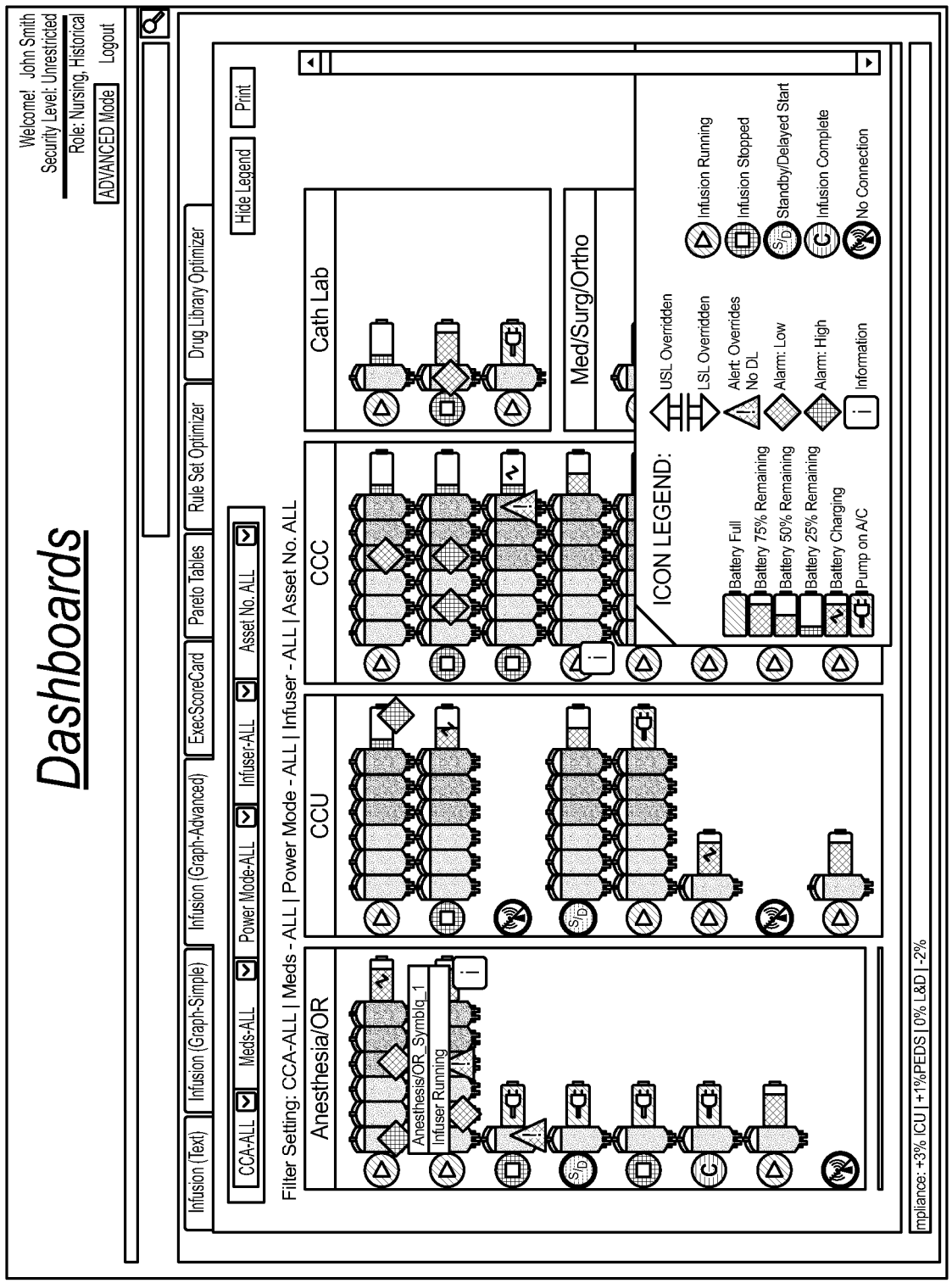
FIG. 8 illustrates an example screen shot of the graphical interface shown in FIG. 7 with additional associated information.

Using a pointer device, hovering over any of the icons in FIG. 7 may provide additional real-time information, such as shown in FIG. 8. Hovering over an icon causes the graphical representation to produce a pop-up screen containing more specific information on the infuser, the wired or wireless network, the medication order, the medication in the container, or the patient.

An example screen shot of the ExecScoreCard tab is shown in FIG. 9. Data in this interface is more historical in nature and may be filtered per time period, per infusion pump, or per clinical care area. The dashboard may generate the executive scorecard data from the raw Hospira MedNet™ database. The executive scorecard produces actionable, sorted data providing focus in identifying medication delivery trends and clinical best practice variations and potential issues. Categories are displayed in "Top 10" format and include medications causing the most alerts overall, medications causing the most overrides, edits and medications causing the most hard limit alerts. The example shown in FIG. 9 displays a summary at the top for all CCAs and all infusers for a selected period of time, which includes but is not limited to Drug Library compliance, total number of programs, total number of alerts, overrides, edits, etc. The example then displays the "Top 10" medications causing alerts; summarizing total programs, alerts, % of alerts to programs, number of overrides and number of edits. If a user would like to investigate a specific medication (in our example Propofol), clicking on the red "+" allows the clinician to view the data related to Propofol down to the individual program and infusion level. The result of this "drill down" is illustrated as a pop-up overlay in FIG. 10. The user can view each individual program involving the chosen medication (in our example, Propofol), including alert date and time, the type of limit violated, the numeric value of the limit as well as the initial and final dose entered by the clinician on the infusion device. Filters allow a user to focus and narrow metrics, namely the filters include: clinical care area, infuser type (e.g., all, PLUM A+™ SYMBIQ™, LIFECARE PCA™, SMITHS MEDICAL MEDFUSION™, ALARIS MEDLEY™, B. BRAUN OUTLOOK™, SIGMA™, etc.), and a date-range of the report. FIG. 11 is an example screen shot to filter the data by a date-range. Sorting buttons are provided at the top of each column of data in FIG. 11 to allow the user to sort the data displayed alphabetically, alphanumerically or numerically, if desired. It will be appreciated that such sorting buttons are contemplated to be used on other tables of data shown in the figures and discussed herein.

Figure 12:
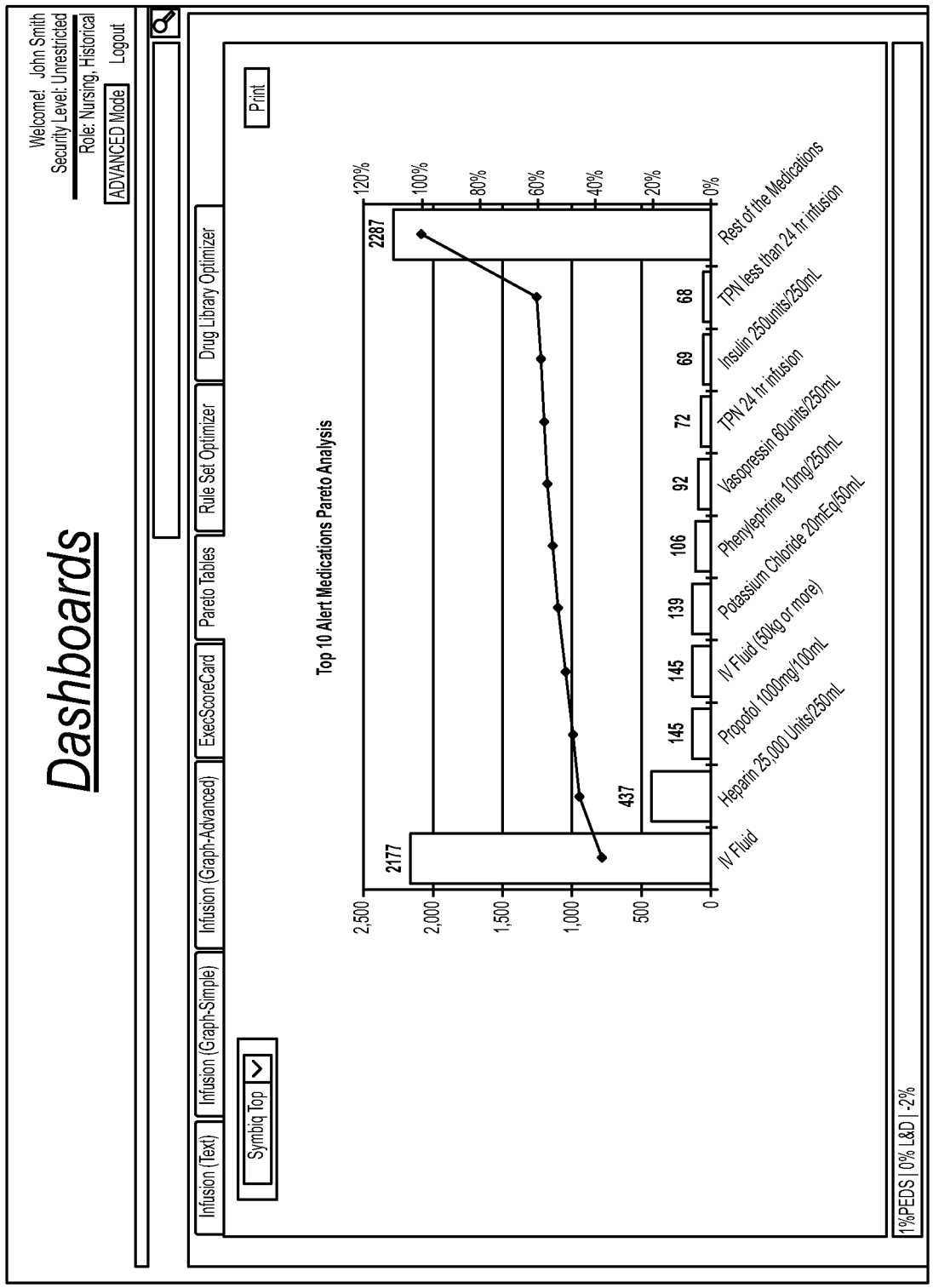
FIG. 12 illustrates an example screen shot of the data seen in FIG. 9 in a graphical format as a Pareto analysis chart or table.

An example screen shot of the Pareto analysis chart is shown in FIG. 12. The Pareto chart is the graphical display of the numeric data presented in the executive scorecard, showing individual values compared to a cumulative total. Any filter that has been applied in the generation of the executive scorecard will apply to or update the Pareto table. Furthermore, where the "ALL" filter has been used to generate the executive scorecard, additional filtering can be used or enabled for the Pareto chart. For example, if the ALL CCA/ALL Infuser executive scorecard from FIG. 11 is used as the starting point, the Pareto chart in FIG. 12 can be prepared for a filtered set of "ALL CCA" data in which a SYMBIQ infusion system is the selected infuser type. The purpose of the Pareto chart is to highlight the most important among a (typically large) set of factors. The Pareto principle (also known as the 80-20 rule) states that, for many events, roughly 80% of the effects come from 20% of the causes. Applied to the hospital environment and specifically medication administration—roughly 20% of the Medications in the Drug Library will cause 80% of the alerts. Review of the Pareto chart will allow the user to save time by focusing on just a few medications when investigating deviations from established best practices. At the same time this investigation will be significant and efficient in that it will address a large number of alerts and potential medication administration issues An example screen shot of the rule set optimizer tab is shown in FIGS. 13A-B. The rule set optimizer filters and displays medication-related rule set entries from the drug library of one or more selected infusers and CCAs so that a clinician can review them. A hospital/doctor can enter limits of an amount of a drug that can be administered to provide clinicians a tool to help improve their own environment. Rules may be provided per drug, dose, department of hospital, etc., and may be upper/lower limits on drugs. The rule set optimizer interface may highlight potential sources that may cause unintended edits/overrides. The user is encouraged to review each entry carefully and make any changes as needed using a drug library editing tool such as HOSPIRA MEDNET™ software. Such a tool can be launched from or included with the dashboard. Rules may be provided per drug, dose, department of hospital, etc., and may be upper/lower limits on drugs. The rule set optimizer interface may highlight potential sources that may cause too frequent or unintended edits/overrides. Potential areas for further analysis and improvement include: limits are inconsistent/illogical/overlap, absence of hard limits or alerts, new drug concentration changes, overrides accepted out of habit, instances where nursing staff are pushing drugs more moderately than recommended, etc.

Figure 14:
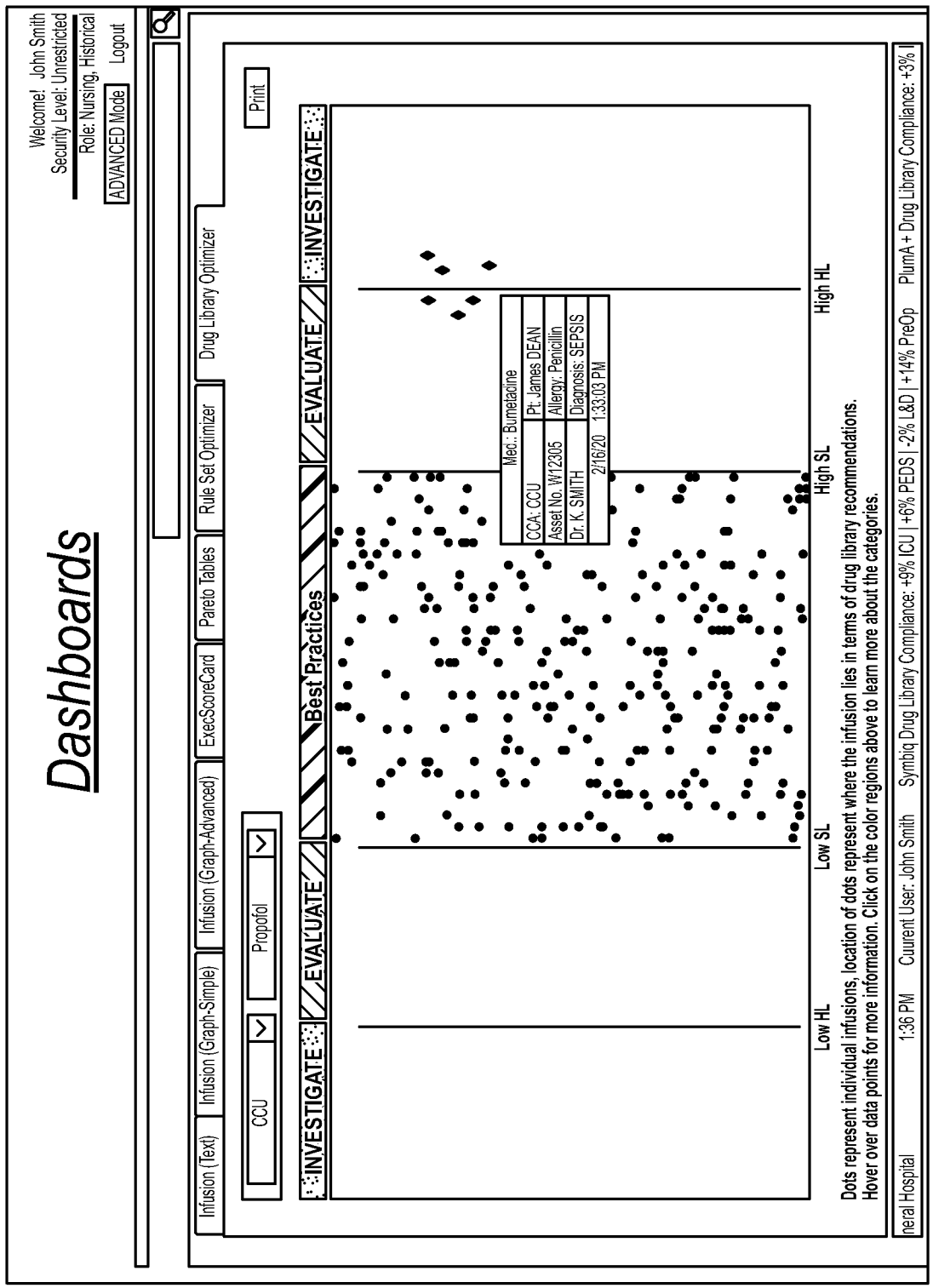

An example screen shot of the drug library optimizer tab is shown in FIG. 14. The drug library optimizer interface displays a histogram of all infusion events, each dot representing an infusion. The clinician is able to see quickly and easily which infusions fall into the hospitals established "best practice" or "green" limits and identify outliers. The outliers are further rated, plotted or spatially arranged by severity into "evaluate-yellow" and "investigate-red" categories. A user may mouse over the dots to see event details (e.g., including a type of medication infused, a clinical care area, an infuser asset number, a clinician and/or physician name, a date and time when event occurred/started, a patient name, allergy information regarding the patient or the medication, and diagnosis).

Events shown within the "best practice" range typically indicate the clinician did not encounter an alert when programming the infusion device. The yellow "evaluate" category would signify soft limit alerts and the red "investigate" category signifies hard limit alerts. Filters (such as CCA and medication) can be applied.

Users with permission access rights may enter alphanumeric type search criteria in the search field located in the upper right portion of the interface, e.g., as shown in the illustration in FIG. 14. For example, an asset number may be entered (i.e., W12305) for an infusion pump, and the dashboard system may search through a database and locate the pump and data pertaining to that pump. Once the dashboard locates the infusion pump, the dashboard may provide the simple graphical tab view, as shown for example in FIG. 15, and may indicate the infusion pump location via a flashing arrow—pointing to the located/identified infusion pump. The user now can hover over, or click-down to drill-down to receive desired information (e.g., alerts, location, asset number, serial number, etc.).

Figure 15:
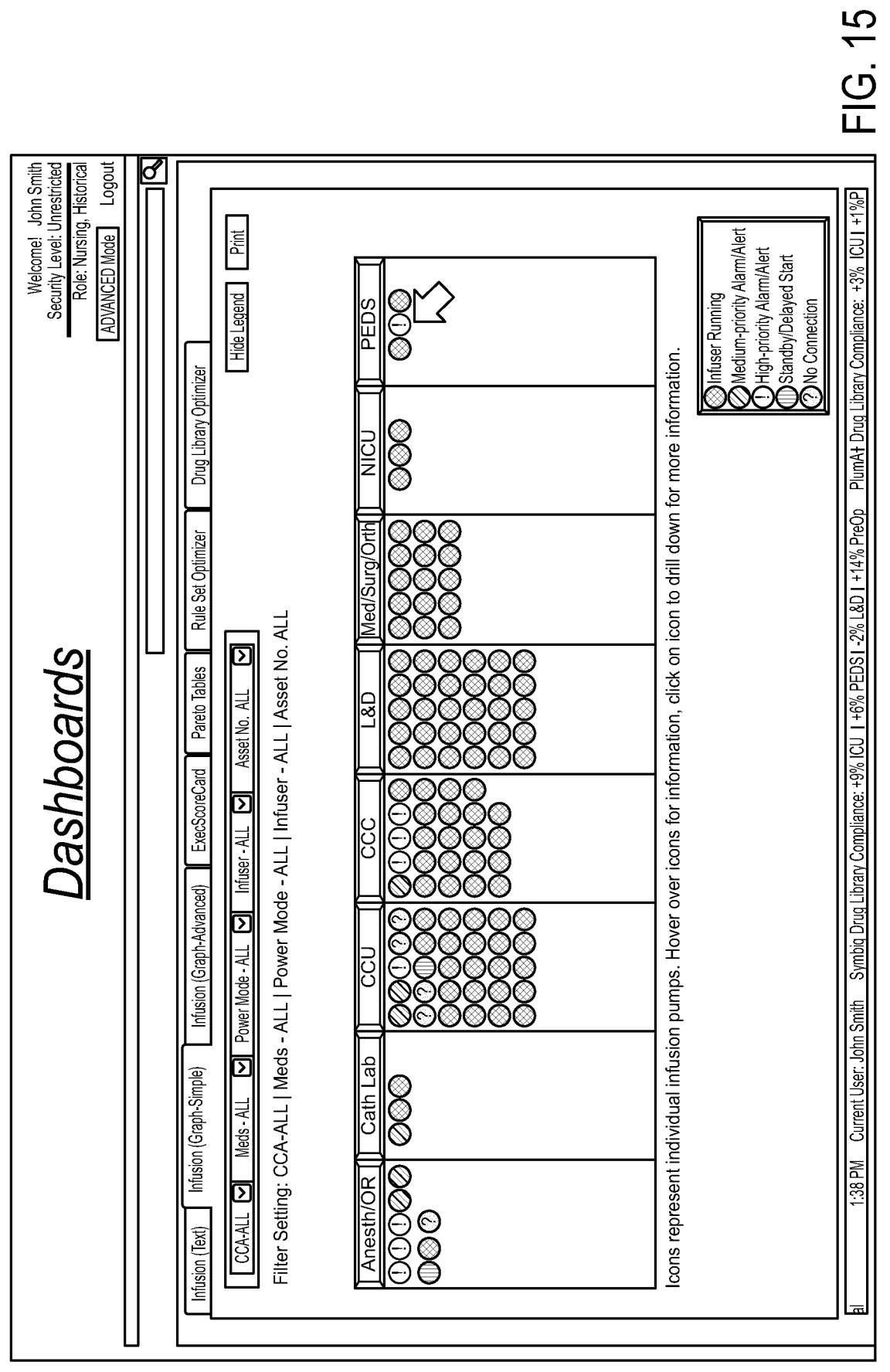

The example interfaces shown in FIGS. 14-15 enable a visual representation of medical devices operating conditions (e.g., operating within or outside of predetermined/preset limits). The interface may be configured to provide an alert indicating which medical devices are operating outside optimal conditions. The visual representations further illustrate icons/graphics in a meaningful manner, and the icons/graphics and interface provide functionality as well. For example, a graphical representation of icons of infusion pumps can be organized based on color and location within the interface to provide information to a user (e.g., dots represent infusion pumps/color indicates status, graphically show number of bags of pumps/color indicates channel of pump, dots represent an infusion event (drug library optimizer) to illustrate pumps within range of best practice). Positioning of icons in the graphical representations can provide information to a user and selection of items on or within the interface may provide additional information about the items, such as for example, selection of an icon associated with a medical device may return a map showing the location of the medical device and additional associated information.

In some examples, as shown within any of FIGS. 3-15, the graphical interface representation may include a data scroll at the bottom of the interface to provide various types of information about the hospital, user, time and date, operation of medical devices, such as trends in Drug Library compliance, etc.

Within examples described herein, a graphical interface platform is provided that receives data and provides reports in real-time and on a historical or trended basis to users. The graphical interface may be configured to determine medical devices operating outside of protocol, and may be configured according to filter parameters. For example, ad-hoc research may be performed by configuring filters of the graphical interface to determine operation of devices, administration of medications, etc. As a specific example, a user may research for trending in the past twenty-four hour period for usage of the drug heparin within a certain unit of a hospital. With regard to operating outside of protocol, a user can determine top ten errors or adverse events within a hospital.

The graphical interface may be configured to process received data to provide trending in real-time, such as nursing function oversight or why a dose of medication was prescribed when outside certain protocols. In examples, the interface may enable hospital personnel to readily identify infusion pumps that are operating outside of protocol or to identify practice trends regarding the use of pumps.

The graphical interface further enables CQI (continuous quality improvement) reporting, providing actionable data to support the caregiver at the bedside, improve medication administration safety and to avoid ADE's (adverse drug events) and potential patient harm. The graphical interface supports the user in identifying opportunity for drug library optimization.

The graphical interface may be further configured to provide notifications for any number of indicators, alerts, and alarms. The notifications can be provided in an escalated manner, such as to initially provide the notification to the bedside nurse, then to the charge nurse, then to the house or facility supervisor, etc.

The graphical interface may be further configured to enable searching for data, such as to search for a specific medical device and return a location of the device, information associated with use of the device, etc. The graphical interface may receive data from a number of systems in a hospital, and provide information related to census and patient acuity, ensuring the correct distribution and availability of infusion devices, etc. Further, the graphical interface may be configured to provide a two-dimensional or three-dimensional map of where a medical device is located. The map can include graphical representations of the medical devices in a particular area or volume of space. The graphical representations can be relatively simple geometric shapes such as dots, triangles or rectangles representing different medical devices or they may be digital or holographic images of the medical devices. As described herein the graphical representations of the medical devices on the map can be equipped with colors, text, symbols or other display characteristics that provide additional information, including but not limited to battery/AC status, alert/alarm status, no connection status, etc.

The graphical interface may be accessible via the Internet, an intranet or other web-based application. The graphical interface may be configured as shown in any of the examples described herein to provide a graphical representation of medical devices in which the graphical representation indicates information about the medical devices using color, icons, location of graphics, etc.

Within examples described herein, a graphical interface platform is provided that illustrates a number of types of information. Components of the graphical interface platform may be customizable in a drag/drop manner, such that components of the graphical interface platform include modules for display. For example, drag-and-drop includes action of (or support for the action of) selecting an object and dragging the object to a location in the interface or onto another object. Objects to be selected may include components of the graphical interface platform. The components of the graphical interface platform include any of the illustrations within FIGS. 3-15. For example, components may include the high-level infuser information shown in the table in FIG. 3, the columns of graphical illustrations shown in FIGS. 4-8 and FIG. 15, the executive scorecard tables shown in FIGS. 9-11, the Pareto table or chart shown in FIG. 12, the rule-set optimizer information tables shown in FIGS. 13A-B, or the columns of data as illustrated in FIG. 14. Thus, the graphical interface platform may be customizable to illustrate any number or combination of data as shown in any of FIGS. 3-15, for example.

It is further contemplated that the dashboard or graphical interface platform can be arranged to be customizable or configurable by the user to define the screens and screen content they find most relevant or helpful in their role. It should also be understood that while a "Top 10" approach has been taken on some screens, one or more approaches selected from a top 3, 5, 15, 20, 25, 50 or 100 approach could be implemented instead or as well.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Furthermore, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

What is claimed is:

1. A method of displaying information from a plurality of infusion pump systems on a display, the method comprising:
   generating a first user interface, the first user interface comprising:
      a plurality of columns corresponding to a plurality of specific areas in a hospital, each column corresponding to a different specific area in the hospital,
   wherein each of the plurality of columns comprises:
      a plurality of icons graphically representing a plurality of infusion pump systems located in the specific area associated with a respective column, each of the plurality of icons corresponding to a status of a respective infusion pump system, each of the plurality of infusion pump systems configured to provide a fluid.

2. The method of claim 1, wherein each of the plurality of icons comprises a circular dot.

3. The method of claim 1, wherein each of the plurality of icons comprises a first symbol indicating a respective infusion pump system is running, a second symbol indicating the respective infusion pump system is stopped, a third symbol indicating the respective infusion pump system is on standby or delayed start, a fourth symbol indicating the respective infusion pump system has completed infusion, or a fifth symbol indicating the respective infusion pump system is offline or not connected.

4. The method of claim 1, wherein each of the plurality of icons comprises a first symbol indicating a respective infusion pump system is running, a second symbol indicating the respective infusion pump system has a high alert, a third symbol indicating the respective infusion pump system has a medium alert, a fourth symbol indicating the respective infusion pump system is on standby or delayed start, or a fifth symbol indicating the respective infusion pump system is offline or not connected.

5. The method of claim 1, wherein each of the plurality of columns is configured to be filtered by a medication type, a power mode, a type of infuser, or an asset number.

6. The method of claim 1, wherein the first user interface further comprises a pop-up screen containing information related to the status of the infusion pump system, an identification of a caregiver, or further information related to the infusion pump system.

7. The method of claim 6, wherein the further information related to the infusion pump system comprises an infuser name, a drug library in use, an alert status, a battery life, an alarm status, a length of time of the alarm status, or a type of medication.

8. The method of claim 1, wherein a color or a pattern of each of the plurality of icons indicates the status of a respective infusion pump system.

9. The method of claim 1, further comprising a location symbol associated with an infusion pump system which has been selected or searched.

10. The method of claim 9, wherein the location symbol comprises a flashing symbol.

11. A system configured to display information associated with a plurality of infusion pump systems, the system comprising one or more hardware processors configured to:
generate a first graphical interface comprising a plurality of columns corresponding to a plurality of specific areas in a hospital, each column of the plurality of columns corresponding to a different specific area in the hospital wherein each of the plurality of columns comprises:
a plurality of icons graphically representing a plurality of infusion pump systems located in the specific area associated with a respective column, each of the plurality of icons corresponding to a status of a respective infusion pump system, each of the plurality of infusion pump systems configured to provide a fluid; and
provide the first graphical interface on a computer display.

12. The system of claim 11, wherein each of the plurality of icons comprises a circular dot.

13. The system of claim 11, wherein each of the plurality of icons comprises a first symbol indicating a respective infusion pump system is running, a second symbol indicating the respective infusion pump system is stopped, a third symbol indicating the respective infusion pump system is on standby or delayed start, a fourth symbol indicating the respective infusion pump system has completed infusion, or a fifth symbol indicating the respective infusion pump system is offline or not connected.

14. The system of claim 11, wherein each of the plurality of icons comprises a first symbol indicating a respective infusion pump system is running, a second symbol indicating the respective infusion pump system has a high alert, a third symbol indicating the respective infusion pump system has a medium alert, a fourth symbol indicating the respective infusion pump system is on standby or delayed start, or a fifth symbol indicating the respective infusion pump system is offline or not connected.

15. The system of claim 11, wherein each of the plurality of columns is configured to be filtered by a medication type, a power mode, a type of infuser, or an asset number.

16. The system of claim 11, wherein the first graphical interface further comprises a pop-up screen containing information related to the status of the infusion pump system, an identification of a caregiver, or further information related to the infusion pump system.

17. The system of claim 16, wherein the further information related to the infusion pump system comprises an infuser name, a drug library in use, an alert status, a battery life, an alarm status, a length of time of the alarm status, or a type of medication.

18. The system of claim 11, wherein a color or a pattern of each of the plurality of icons indicates the status of a respective infusion pump system.

* * * * *

UNITED STATES PATENT AND TRADEMARK OFFICE
CERTIFICATE OF CORRECTION

PATENT NO. : 11,599,854 B2
APPLICATION NO. : 17/225911
DATED : March 7, 2023
INVENTOR(S) : James A. Hume It is certified that error appears in the above-identified patent and that said Letters Patent is hereby corrected as shown below:

On the Title Page

Column 1, Line 2, under Inventors, delete "Heighls," and insert --Heights,--.

On Page 8, Column 2, Line 27, under U.S. Patent Documents, delete "Row" and insert --Fangrow--.

On Page 8, Column 2, Line 64, under U.S. Patent Documents, delete "Row" and insert --Fangrow--.

On Page 14, Column 1, Line 36, under Other Publications, delete "eom" and insert --com--.

In the Claims

In Column 17, Claim 11, Line 42, delete "hospital" and insert --hospital,--.

Signed and Sealed this
Twentieth Day of June, 2023

*Katherine Kelly Vidal*

Katherine Kelly Vidal
*Director of the United States Patent and Trademark Office*